(12) United States Patent
Neisz et al.

(10) Patent No.: US 9,757,264 B2
(45) Date of Patent: Sep. 12, 2017

(54) DEVICES AND METHODS FOR GASTROINTESTINAL BYPASS

(71) Applicant: ValenTx, Inc., Carpinteria, CA (US)

(72) Inventors: Johann Neisz, Minneapolis, MN (US); Cole Chen, Ventura, CA (US)

(73) Assignee: ValenTx, Inc., Maple Grove, MN (US)

( * ) Notice: Subject to any disclaimer, the term of this patent is extended or adjusted under 35 U.S.C. 154(b) by 0 days.

(21) Appl. No.: 14/208,642

(22) Filed: Mar. 13, 2014

(65) Prior Publication Data
US 2014/0276333 A1    Sep. 18, 2014

Related U.S. Application Data

(60) Provisional application No. 61/780,777, filed on Mar. 13, 2013.

(51) Int. Cl.
*A61F 5/00*    (2006.01)

(52) U.S. Cl.
CPC .......... *A61F 5/0076* (2013.01); *A61F 5/0079* (2013.01)

(58) Field of Classification Search
CPC .............................. A61F 5/0076; A61F 5/0079
See application file for complete search history.

(56) References Cited

U.S. PATENT DOCUMENTS

| | | |
|---|---|---|
| 3,357,432 A | 12/1967 | Sparks |
| 3,589,356 A | 6/1971 | Silverman |
| 3,982,544 A | 9/1976 | Dyck |
| 4,006,747 A | 2/1977 | Kronenthal et al. |

(Continued)

FOREIGN PATENT DOCUMENTS

| | | |
|---|---|---|
| EP | 0817598 B1 | 1/1998 |
| EP | 1237501 B1 | 9/2002 |

(Continued)

OTHER PUBLICATIONS

U.S. Appl. No. 14/987,398 dated Jan. 4, 2016, Thompson et al.

(Continued)

*Primary Examiner* — Tatyana Zalukaeva
*Assistant Examiner* — Benjamin Klein
(74) *Attorney, Agent, or Firm* — Jinn Su

(57) ABSTRACT

A gastrointestinal bypass device for directing food and liquids from an esophagus and/or a proximal portion of a stomach into an intestines is described. The device comprises a receiver, a sleeve, and a device coupling. The receiver may be configured to be positioned in the esophagus and/or the stomach. A proximal portion of the receiver may be configured to open and close to at least partially conform to an inside of the esophagus and/or a proximal portion of the stomach. The receiver may be configured to receive food and liquids from the esophagus and/or a proximal portion of the stomach into a lumen of the receiver. The sleeve may be coupled to a distal portion of the receiver. The sleeve may be configured to be positioned in the stomach and the intestines. The sleeve may have a lumen in communication with the lumen of the receiver. The sleeve may be configured to direct the food and the liquids from the receiver into the intestines. The device coupling may be coupled to the distal portion of the receiver and/or a proximal portion of the sleeve. The device coupling may be configured to be coupled to one or more tissue anchors.

13 Claims, 28 Drawing Sheets

(56) References Cited

U.S. PATENT DOCUMENTS

| | | |
|---|---|---|
| 4,043,345 A | 8/1977 | Kramann et al. |
| 4,109,659 A | 8/1978 | Sheridan |
| 4,133,315 A | 1/1979 | Berman et al. |
| 4,134,405 A | 1/1979 | Smit |
| 4,217,664 A | 8/1980 | Faso |
| 4,235,238 A | 11/1980 | Ogiu et al. |
| 4,252,131 A | 2/1981 | Hon et al. |
| 4,271,839 A | 6/1981 | Fogarty et al. |
| 4,315,509 A | 2/1982 | Smit |
| 4,329,995 A | 5/1982 | Anthracite |
| 4,416,267 A | 11/1983 | Garren et al. |
| 4,493,711 A | 1/1985 | Chin et al. |
| 4,501,264 A | 2/1985 | Rockey |
| 4,532,926 A | 8/1985 | O'Holla |
| 4,606,347 A | 8/1986 | Fogarty et al. |
| 4,613,323 A | 9/1986 | Norton et al. |
| 4,630,609 A | 12/1986 | Chin |
| 4,641,653 A | 2/1987 | Rockey |
| 4,719,916 A | 1/1988 | Ravo |
| 4,763,653 A | 8/1988 | Rockey |
| 4,826,481 A | 5/1989 | Sacks et al. |
| 4,846,836 A | 7/1989 | Reich |
| 4,863,440 A | 9/1989 | Chin |
| 4,905,693 A | 3/1990 | Ravo |
| 4,946,440 A | 8/1990 | Hall |
| 5,085,661 A | 2/1992 | Moss |
| 5,104,399 A | 4/1992 | Lazarus |
| RE34,021 E | 8/1992 | Mueller et al. |
| 5,171,305 A | 12/1992 | Schickling et al. |
| 5,236,423 A | 8/1993 | Mix et al. |
| 5,269,809 A | 12/1993 | Hayhurst et al. |
| 5,306,300 A | 4/1994 | Berry |
| 5,314,473 A | 5/1994 | Godin |
| 5,318,530 A | 6/1994 | Nelson, Jr. |
| 5,411,508 A | 5/1995 | Bessler et al. |
| 5,425,765 A | 6/1995 | Tiefenbrun et al. |
| 5,431,666 A | 7/1995 | Sauer et al. |
| 5,443,499 A | 8/1995 | Schmitt |
| 5,458,573 A | 10/1995 | Summers |
| 5,470,337 A | 11/1995 | Moss |
| 5,503,634 A | 4/1996 | Christy |
| 5,582,616 A | 12/1996 | Bolduc et al. |
| 5,613,975 A | 3/1997 | Christy |
| 5,645,568 A | 7/1997 | Chervitz et al. |
| 5,676,688 A | 10/1997 | Jaker et al. |
| 5,681,324 A | 10/1997 | Kammerer et al. |
| 5,695,517 A | 12/1997 | Marin et al. |
| 5,785,684 A | 7/1998 | Zimmon |
| 5,807,303 A | 9/1998 | Bays |
| 5,820,584 A | 10/1998 | Crabb |
| 5,824,008 A | 10/1998 | Bolduc et al. |
| 5,824,036 A | 10/1998 | Lauterjung |
| 5,843,164 A | 12/1998 | Frantzen et al. |
| 5,861,036 A | 1/1999 | Godin |
| 5,887,594 A | 3/1999 | LoCicero, III |
| 5,957,940 A | 9/1999 | Tanner et al. |
| 5,972,023 A | 10/1999 | Tanner et al. |
| 5,997,556 A | 12/1999 | Tanner |
| 6,007,544 A | 12/1999 | Kim |
| 6,066,146 A | 5/2000 | Carroll et al. |
| 6,113,609 A | 9/2000 | Adams |
| 6,159,158 A | 12/2000 | Lowe |
| 6,193,733 B1 | 2/2001 | Adams |
| 6,206,895 B1 | 3/2001 | Levinson |
| 6,250,922 B1 | 6/2001 | Bassett et al. |
| 6,254,642 B1 | 7/2001 | Taylor |
| 6,264,700 B1 | 7/2001 | Kilcoyne et al. |
| 6,285,897 B1 | 9/2001 | Kilcoyne et al. |
| 6,302,917 B1 | 10/2001 | Dua et al. |
| 6,309,343 B1 | 10/2001 | Lentz et al. |
| 6,312,437 B1 | 11/2001 | Kortenbach |
| 6,338,345 B1 | 1/2002 | Johnson et al. |
| 6,387,104 B1 | 5/2002 | Pugsley, Jr. et al. |
| 6,402,780 B2 | 6/2002 | Williamson, IV et al. |
| 6,409,656 B1 | 6/2002 | Sangouard et al. |
| 6,432,064 B1 | 8/2002 | Hibner et al. |
| 6,447,533 B1 | 9/2002 | Adams |
| 6,464,707 B1 | 10/2002 | Bjerken |
| 6,494,888 B1 | 12/2002 | Laufer et al. |
| 6,520,974 B2 | 2/2003 | Tanner et al. |
| 6,535,764 B2 | 3/2003 | Imran et al. |
| 6,544,291 B2 | 4/2003 | Taylor |
| 6,558,400 B2 | 5/2003 | Deem et al. |
| 6,558,429 B2 | 5/2003 | Taylor |
| 6,592,596 B1 | 7/2003 | Geitz |
| 6,595,911 B2 | 7/2003 | LoVuolo |
| 6,626,916 B1 | 9/2003 | Yeung et al. |
| 6,626,919 B1 | 9/2003 | Swanstrom |
| 6,635,066 B2 | 10/2003 | Tanner et al. |
| 6,675,809 B2 | 1/2004 | Stack et al. |
| 6,692,506 B1 | 2/2004 | Ory et al. |
| 6,699,263 B2 | 3/2004 | Cope |
| 6,702,735 B2 | 3/2004 | Kelly |
| 6,736,828 B1 | 5/2004 | Adams et al. |
| 6,740,121 B2 | 5/2004 | Geitz |
| 6,746,489 B2 | 6/2004 | Dua et al. |
| 6,764,518 B2 | 7/2004 | Godin |
| 6,773,452 B2 | 8/2004 | Shaker |
| 6,790,237 B2 | 9/2004 | Stinson |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,344 B2 | 5/2006 | Kagan et al. |
| 7,083,629 B2 | 8/2006 | Weller et al. |
| 7,097,665 B2 | 8/2006 | Stack et al. |
| 7,111,627 B2 | 9/2006 | Stack et al. |
| 7,120,498 B2 | 10/2006 | Imran et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,175,669 B2 | 2/2007 | Geitz |
| RE39,533 E | 3/2007 | Ranoux |
| 7,211,114 B2 | 5/2007 | Bessler et |
| 7,220,237 B2 | 5/2007 | Gannoe et al. |
| 7,220,284 B2 | 5/2007 | Kagan et al. |
| 7,229,428 B2 | 6/2007 | Gannoe et al. |
| 7,244,270 B2 | 7/2007 | Lesh |
| 7,267,694 B2 | 9/2007 | Levine et al. |
| 7,288,099 B2 | 10/2007 | Deem et al. |
| 7,288,101 B2 | 10/2007 | Deem et al. |
| 7,306,614 B2 | 12/2007 | Weller et al. |
| 7,309,341 B2 | 12/2007 | Ortiz et al. |
| 7,314,489 B2 | 1/2008 | McKenna et al. |
| 7,316,716 B2 | 1/2008 | Egan |
| 7,329,285 B2 | 2/2008 | Levine et al. |
| 7,338,505 B2 | 3/2008 | Belson |
| 7,347,868 B2 | 3/2008 | Burnett et al. |
| 7,347,875 B2 | 3/2008 | Levine et al. |
| 7,354,454 B2 | 4/2008 | Stack et al. |
| 7,361,180 B2 | 4/2008 | Saadat et al. |
| 7,371,215 B2 | 5/2008 | Colliou et al. |
| 7,390,329 B2 | 6/2008 | Westra et al. |
| 7,416,554 B2 | 8/2008 | Lam et al. |
| 7,431,725 B2 | 10/2008 | Stack et al. |
| 7,468,060 B2 | 12/2008 | Utley et al. |
| 7,476,256 B2 | 1/2009 | Meade et al. |
| 7,483,754 B2 | 1/2009 | Imran et al. |
| 7,509,175 B2 | 3/2009 | Sparks et al. |
| 7,520,884 B2 | 4/2009 | Swanstrom et al. |
| 7,571,729 B2 | 8/2009 | Saadat et al. |
| 7,615,064 B2 | 11/2009 | Bjerken |
| 7,628,821 B2 | 12/2009 | Stack et al. |
| 7,666,180 B2 | 2/2010 | Holsten et al. |
| 7,678,068 B2 | 3/2010 | Levine et al. |
| 7,678,135 B2 | 3/2010 | Maahs et al. |
| 7,682,330 B2 | 3/2010 | Meade et al. |
| 7,703,459 B2 | 4/2010 | Saadat et al. |
| 7,704,261 B2 | 4/2010 | Sakamoto et al. |
| 7,704,264 B2 | 4/2010 | Ewers et al. |
| 7,708,684 B2 | 5/2010 | Demarais et al. |
| 7,736,374 B2 | 6/2010 | Vaughan et al. |

(56) References Cited

U.S. PATENT DOCUMENTS

| | | |
|---|---|---|
| 7,736,378 B2 | 6/2010 | Maahs et al. |
| 7,753,870 B2 | 7/2010 | Demarais et al. |
| 7,766,973 B2 | 8/2010 | Levine et al. |
| 7,780,592 B2 | 8/2010 | Tronnes |
| 7,794,447 B2 | 9/2010 | Dann et al. |
| 7,815,589 B2 | 10/2010 | Meade et al. |
| 7,833,280 B2 | 11/2010 | Stack et al. |
| 7,837,669 B2 | 11/2010 | Dann et al. |
| 7,841,978 B2 | 11/2010 | Gertner |
| 7,846,138 B2 | 12/2010 | Dann et al. |
| 7,881,797 B2 | 2/2011 | Griffin et al. |
| 7,892,214 B2 | 2/2011 | Kagan et al. |
| 7,935,073 B2 | 5/2011 | Levine et al. |
| 7,942,884 B2 | 5/2011 | Vahid et al. |
| 7,981,162 B2 | 7/2011 | Stack et al. |
| 8,012,135 B2 | 9/2011 | Dann et al. |
| 8,012,140 B1 | 9/2011 | Kagan et al. |
| 8,020,741 B2 | 9/2011 | Cole et al. |
| 8,029,455 B2 | 10/2011 | Stack et al. |
| 8,034,063 B2 | 10/2011 | Binmoeller |
| 8,070,743 B2 | 12/2011 | Kagan et al. |
| 8,083,758 B2 | 12/2011 | Hsu et al. |
| 8,096,966 B2 | 1/2012 | Levine et al. |
| 8,100,925 B2 | 1/2012 | Hsu et al. |
| 8,105,342 B2 | 1/2012 | Onuki et al. |
| 8,118,767 B2 | 2/2012 | Laufer |
| 8,118,774 B2 | 2/2012 | Dann et al. |
| 8,147,441 B2 | 4/2012 | Gannoe et al. |
| 8,182,441 B2 | 5/2012 | Swain et al. |
| 8,182,459 B2 | 5/2012 | Dann et al. |
| 8,206,417 B2 | 6/2012 | Maahs et al. |
| 8,206,456 B2 | 6/2012 | Stack et al. |
| 8,211,186 B2 | 7/2012 | Belhe et al. |
| 8,257,374 B2 | 9/2012 | Hsu et al. |
| 8,282,598 B2 | 10/2012 | Belhe et al. |
| 8,298,291 B2 | 10/2012 | Ewers et al. |
| 8,303,669 B2 | 11/2012 | Meade et al. |
| 8,372,158 B2 | 2/2013 | Levy et al. |
| 8,376,981 B2 | 2/2013 | Laufer |
| 8,382,800 B2 | 2/2013 | Maahs et al. |
| 8,425,451 B2 | 4/2013 | Levine et al. |
| 8,444,657 B2 | 5/2013 | Saadat et al. |
| 8,702,641 B2 | 4/2014 | Belhe et al. |
| 8,808,270 B2 | 8/2014 | Dann et al. |
| 8,956,318 B2 | 2/2015 | Miller et al. |
| 8,968,270 B2 | 3/2015 | Kagan et al. |
| 9,039,649 B2 | 5/2015 | Neisz et al. |
| 9,050,168 B2 | 6/2015 | Neisz et al. |
| 9,060,844 B2 | 6/2015 | Kagan et al. |
| 9,173,759 B2 | 11/2015 | Nelson et al. |
| 9,265,596 B2 | 2/2016 | Shank et al. |
| 2001/0016748 A1 | 8/2001 | Tanner et al. |
| 2001/0020189 A1 | 9/2001 | Taylor |
| 2001/0020190 A1 | 9/2001 | Taylor |
| 2001/0044595 A1 | 11/2001 | Reydel et al. |
| 2001/0056282 A1 | 12/2001 | Sonnenschein et al. |
| 2002/0016607 A1 | 2/2002 | Bonadio et al. |
| 2002/0026214 A1 | 2/2002 | Tanner et al. |
| 2002/0035370 A1 | 3/2002 | Kortenbach |
| 2002/0040226 A1 | 4/2002 | Laufer et al. |
| 2002/0058960 A1 | 5/2002 | Hudson et al. |
| 2002/0082621 A1 | 6/2002 | Schurr et al. |
| 2002/0111658 A1 | 8/2002 | Greenberg et al. |
| 2002/0143387 A1 | 10/2002 | Soetikno et al. |
| 2002/0165589 A1 | 11/2002 | Imran et al. |
| 2002/0183768 A1 | 12/2002 | Deem et al. |
| 2002/0188344 A1 | 12/2002 | Bolea et al. |
| 2002/0188354 A1 | 12/2002 | Peghini |
| 2002/0198588 A1 | 12/2002 | Armstrong et al. |
| 2003/0014064 A1 | 1/2003 | Blatter |
| 2003/0018358 A1 | 1/2003 | Saadat |
| 2003/0040804 A1 | 2/2003 | Stack et al. |
| 2003/0040808 A1 | 2/2003 | Stack et al. |
| 2003/0055313 A1 | 3/2003 | Anderson et al. |
| 2003/0055442 A1 | 3/2003 | Laufer et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120285 A1 | 6/2003 | Kortenbach |
| 2003/0120292 A1 | 6/2003 | Park et al. |
| 2003/0130560 A1 | 7/2003 | Suzuki et al. |
| 2003/0130561 A1 | 7/2003 | Suzuki et al. |
| 2003/0139752 A1 | 7/2003 | Pasricha et al. |
| 2003/0171775 A1 | 9/2003 | Belson |
| 2003/0176912 A1 | 9/2003 | Chuter et al. |
| 2003/0181929 A1 | 9/2003 | Geitz |
| 2003/0191497 A1 | 10/2003 | Cope |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2004/0002734 A1 | 1/2004 | Fallin et al. |
| 2004/0006351 A1 | 1/2004 | Gannoe et al. |
| 2004/0024427 A1 | 2/2004 | Imran et al. |
| 2004/0039250 A1 | 2/2004 | Tholfsen et al. |
| 2004/0039452 A1 | 2/2004 | Bessler |
| 2004/0044364 A1 | 3/2004 | DeVries et al. |
| 2004/0059349 A1 | 3/2004 | Sixto, Jr. et al. |
| 2004/0059354 A1 | 3/2004 | Smith et al. |
| 2004/0082963 A1 | 4/2004 | Gannoe et al. |
| 2004/0087976 A1 | 5/2004 | DeVries et al. |
| 2004/0087977 A1 | 5/2004 | Nolan et al. |
| 2004/0088023 A1 | 5/2004 | Imran et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0097986 A1 | 5/2004 | Adams |
| 2004/0097987 A1 | 5/2004 | Pugsley et al. |
| 2004/0102855 A1 | 5/2004 | Shank |
| 2004/0107004 A1* | 6/2004 | Levine ............... A61B 17/0401 623/23.64 |
| 2004/0116949 A1 | 6/2004 | Ewers et al. |
| 2004/0117031 A1 | 6/2004 | Stack et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0133089 A1 | 7/2004 | Kilcoyne et al. |
| 2004/0133147 A1 | 7/2004 | Woo |
| 2004/0133219 A1 | 7/2004 | Forsell |
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0138761 A1 | 7/2004 | Stack et al. |
| 2004/0143342 A1 | 7/2004 | Stack et al. |
| 2004/0147958 A1 | 7/2004 | Lam et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0172142 A1 | 9/2004 | Stack et al. |
| 2004/0176799 A1 | 9/2004 | Chanduszko et al. |
| 2004/0181242 A1 | 9/2004 | Stack et al. |
| 2004/0186514 A1 | 9/2004 | Swain et al. |
| 2004/0193190 A1 | 9/2004 | Liddicoat et al. |
| 2004/0199189 A1 | 10/2004 | Gifford, III et al. |
| 2004/0204768 A1 | 10/2004 | Geitz |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243195 A1 | 12/2004 | Imran et al. |
| 2004/0249362 A1 | 12/2004 | Levine et al. |
| 2004/0249367 A1 | 12/2004 | Saadat et al. |
| 2005/0033240 A1 | 2/2005 | Oishi et al. |
| 2005/0033330 A1 | 2/2005 | Vargas et al. |
| 2005/0033331 A1 | 2/2005 | Burnett et al. |
| 2005/0033332 A1 | 2/2005 | Burnett |
| 2005/0043749 A1 | 2/2005 | Breton et al. |
| 2005/0043757 A1 | 2/2005 | Arad et al. |

(56) References Cited

U.S. PATENT DOCUMENTS

| | | |
|---|---|---|
| 2005/0049718 A1 | 3/2005 | Dann et al. |
| 2005/0055039 A1 | 3/2005 | Burnett et al. |
| 2005/0065401 A1 | 3/2005 | Saadat et al. |
| 2005/0075653 A1 | 4/2005 | Saadat et al. |
| 2005/0075654 A1 | 4/2005 | Kelleher |
| 2005/0080431 A1 | 4/2005 | Levine et al. |
| 2005/0080444 A1 | 4/2005 | Kraemer et al. |
| 2005/0085787 A1 | 4/2005 | Laufer |
| 2005/0085900 A1 | 4/2005 | Case et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0101977 A1 | 5/2005 | Gannoe et al. |
| 2005/0125020 A1 | 6/2005 | Meade et al. |
| 2005/0125075 A1 | 6/2005 | Meade et al. |
| 2005/0143784 A1 | 6/2005 | Imran |
| 2005/0177181 A1 | 8/2005 | Kagan et al. |
| 2005/0187567 A1 | 8/2005 | Baker et al. |
| 2005/0192629 A1 | 9/2005 | Saadat et al. |
| 2005/0197714 A1 | 9/2005 | Sayet |
| 2005/0197715 A1 | 9/2005 | Kugler et al. |
| 2005/0203547 A1 | 9/2005 | Weller et al. |
| 2005/0222592 A1 | 10/2005 | Gannoe et al. |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0245948 A1 | 11/2005 | Khalaj |
| 2005/0247320 A1 | 11/2005 | Stack et al. |
| 2005/0250984 A1 | 11/2005 | Lam et al. |
| 2005/0251159 A1 | 11/2005 | Ewers et al. |
| 2005/0251176 A1 | 11/2005 | Swanstrom et al. |
| 2005/0251208 A1 | 11/2005 | Elmer et al. |
| 2005/0251209 A1 | 11/2005 | Saadat et al. |
| 2005/0256587 A1 | 11/2005 | Egan |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2005/0267595 A1 | 12/2005 | Chen et al. |
| 2006/0009858 A1 | 1/2006 | Levine et al. |
| 2006/0015125 A1 | 1/2006 | Swain |
| 2006/0020164 A1 | 1/2006 | Butler et al. |
| 2006/0020247 A1 | 1/2006 | Kagan et al. |
| 2006/0020254 A1 | 1/2006 | van Hoffmann |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0135971 A1 | 6/2006 | Swanstrom et al. |
| 2006/0155312 A1 | 7/2006 | Levine et al. |
| 2006/0155375 A1* | 7/2006 | Kagan ............... A61F 5/0076 623/11.11 |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0173422 A1 | 8/2006 | Reydel et al. |
| 2006/0206063 A1 | 9/2006 | Kagan et al. |
| 2006/0206064 A1 | 9/2006 | Kagan et al. |
| 2006/0212052 A1 | 9/2006 | Shin et al. |
| 2006/0217762 A1 | 9/2006 | Maahs et al. |
| 2006/0235446 A1 | 10/2006 | Godin |
| 2006/0247718 A1 | 11/2006 | Starkebaum |
| 2006/0253126 A1 | 11/2006 | Bjerken et al. |
| 2006/0264982 A1 | 11/2006 | Viola et al. |
| 2006/0265021 A1 | 11/2006 | Herbert et al. |
| 2006/0265042 A1 | 11/2006 | Catanese, III et al. |
| 2006/0265082 A1 | 11/2006 | Meade et al. |
| 2006/0287734 A1 | 12/2006 | Stack et al. |
| 2006/0293742 A1 | 12/2006 | Dann et al. |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0016244 A1 | 1/2007 | Behl et al. |
| 2007/0027548 A1 | 2/2007 | Levine et al. |
| 2007/0027549 A1 | 2/2007 | Godin |
| 2007/0032821 A1 | 2/2007 | Chin-Chen et al. |
| 2007/0032879 A1 | 2/2007 | Levine et al. |
| 2007/0083271 A1 | 4/2007 | Levine et al. |
| 2007/0100367 A1 | 5/2007 | Quijano et al. |
| 2007/0100368 A1 | 5/2007 | Quijano et al. |
| 2007/0106233 A1 | 5/2007 | Huang et al. |
| 2007/0106313 A1 | 5/2007 | Golden et al. |
| 2007/0129719 A1 | 6/2007 | Kendale et al. |
| 2007/0149994 A1 | 6/2007 | Sosnowski et al. |
| 2007/0156248 A1 | 7/2007 | Marco et al. |
| 2007/0178160 A1 | 8/2007 | Burnett |
| 2007/0198074 A1 | 8/2007 | Dann et al. |
| 2007/0208360 A1 | 9/2007 | Demarais et al. |
| 2007/0219571 A1 | 9/2007 | Balbierz et al. |
| 2007/0225555 A1 | 9/2007 | Stefanchik |
| 2007/0233162 A1 | 10/2007 | Gannoe et al. |
| 2007/0250132 A1 | 10/2007 | Burnett |
| 2007/0293716 A1 | 12/2007 | Baker et al. |
| 2007/0293885 A1 | 12/2007 | Binmoeller |
| 2008/0004606 A1 | 1/2008 | Swain et al. |
| 2008/0009888 A1 | 1/2008 | Ewers et al. |
| 2008/0033574 A1 | 2/2008 | Bessler et al. |
| 2008/0058840 A1 | 3/2008 | Albrecht et al. |
| 2008/0058887 A1 | 3/2008 | Griffin et al. |
| 2008/0082167 A1 | 4/2008 | Edidin et al. |
| 2008/0103604 A1 | 5/2008 | Levine et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0190989 A1 | 8/2008 | Crews et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0228030 A1 | 9/2008 | Godin |
| 2008/0243071 A1 | 10/2008 | Quijano et al. |
| 2008/0249533 A1 | 10/2008 | Godin |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0269797 A1 | 10/2008 | Stack et al. |
| 2008/0294179 A1 | 11/2008 | Balbierz et al. |
| 2009/0012356 A1 | 1/2009 | Dann et al. |
| 2009/0012541 A1* | 1/2009 | Dahl et al. .................... 606/151 |
| 2009/0012544 A1 | 1/2009 | Thompson et al. |
| 2009/0012553 A1 | 1/2009 | Swain et al. |
| 2009/0018603 A1 | 1/2009 | Mitelberg et al. |
| 2009/0024143 A1 | 1/2009 | Crews et al. |
| 2009/0062881 A1 | 3/2009 | Gross et al. |
| 2009/0125040 A1 | 5/2009 | Hambly et al. |
| 2009/0149871 A9 | 6/2009 | Kagan et al. |
| 2009/0177215 A1 | 7/2009 | Stack et al. |
| 2009/0182355 A1 | 7/2009 | Levine et al. |
| 2009/0182413 A1 | 7/2009 | Burkart et al. |
| 2009/0216337 A1 | 8/2009 | Egan et al. |
| 2010/0016988 A1 | 1/2010 | Stack et al. |
| 2010/0023130 A1 | 1/2010 | Henry et al. |
| 2010/0030017 A1 | 2/2010 | Baker et al. |
| 2010/0049224 A1 | 2/2010 | Vargas |
| 2010/0121462 A1 | 5/2010 | Sobrino-Serrano et al. |
| 2010/0217151 A1 | 8/2010 | Gostout et al. |
| 2010/0256775 A1 | 10/2010 | Belhe et al. |
| 2010/0276469 A1 | 11/2010 | Crews et al. |
| 2010/0280529 A1 | 11/2010 | Crews et al. |
| 2010/0331623 A1 | 12/2010 | Sauer et al. |
| 2011/0004229 A1 | 1/2011 | Priplata et al. |
| 2011/0082471 A1 | 4/2011 | Holcomb et al. |
| 2011/0098630 A1 | 4/2011 | Gagner et al. |
| 2011/0106273 A1 | 5/2011 | Belhe et al. |
| 2011/0125211 A1 | 5/2011 | Griffin et al. |
| 2011/0172584 A1 | 7/2011 | Chin |
| 2011/0213469 A1 | 9/2011 | Chin et al. |
| 2011/0245752 A1 | 10/2011 | Levine et al. |
| 2011/0245854 A1 | 10/2011 | Buxbaum et al. |

(56) References Cited

U.S. PATENT DOCUMENTS

| | | |
|---|---|---|
| 2011/0275912 A1 | 11/2011 | Boyden et al. |
| 2011/0276091 A1 | 11/2011 | Melanson et al. |
| 2011/0319980 A1 | 12/2011 | Ryan |
| 2012/0029413 A1 | 2/2012 | Meade et al. |
| 2012/0029535 A1 | 2/2012 | Swain |
| 2012/0029611 A1 | 2/2012 | Weidman et al. |
| 2012/0053504 A1 | 3/2012 | Kagan et al. |
| 2012/0065571 A1 | 3/2012 | Thompson et al. |
| 2012/0095384 A1 | 4/2012 | Babkes et al. |
| 2012/0184893 A1 | 7/2012 | Thompson et al. |
| 2012/0209164 A1 | 8/2012 | Kagan et al. |
| 2012/0215235 A1 | 8/2012 | Fogel |
| 2012/0232459 A1 | 9/2012 | Dann et al. |
| 2012/0245504 A1 | 9/2012 | Tzvetanov et al. |
| 2012/0253324 A1 | 10/2012 | Lee et al. |
| 2012/0259317 A1 | 10/2012 | Baldwin et al. |
| 2012/0296254 A1 | 11/2012 | Swain et al. |
| 2013/0030351 A1 | 1/2013 | Belhe et al. |
| 2013/0079603 A1 | 3/2013 | Vargas |
| 2013/0184723 A1 | 7/2013 | Swope et al. |
| 2013/0184808 A1 | 7/2013 | Hall et al. |
| 2013/0261368 A1 | 10/2013 | Schwartz |
| 2013/0324902 A1 | 12/2013 | Miller et al. |
| 2013/0324905 A1 | 12/2013 | Nelson et al. |
| 2013/0324926 A1 | 12/2013 | Nelson et al. |
| 2013/0331759 A1* | 12/2013 | Neisz ............... A61F 5/0036 604/8 |
| 2014/0180192 A1 | 6/2014 | Ortiz et al. |
| 2014/0188245 A1 | 7/2014 | Neisz et al. |
| 2014/0358065 A1 | 12/2014 | Dann et al. |
| 2015/0238340 A1 | 8/2015 | Kagan et al. |
| 2015/0366693 A1 | 12/2015 | Kagan et al. |

FOREIGN PATENT DOCUMENTS

| | | |
|---|---|---|
| WO | WO 8000007 A1 | 1/1980 |
| WO | WO 9101117 A1 | 2/1991 |
| WO | WO 96029954 A1 | 10/1996 |
| WO | WO 9856440 A1 | 12/1998 |
| WO | WO 9921490 A1 | 5/1999 |
| WO | WO 9960931 A1 | 5/1999 |
| WO | WO 0012027 A1 | 3/2000 |
| WO | WO 0135834 A1 | 5/2001 |
| WO | WO 0143663 A1 | 6/2001 |
| WO | WO 0183017 A1 | 11/2001 |
| WO | WO 0185034 A1 | 11/2001 |
| WO | WO 0294132 A2 | 11/2002 |
| WO | WO 02102227 A2 | 12/2002 |
| WO | WO 03017882 A2 | 3/2003 |
| WO | WO 03086246 A1 | 10/2003 |
| WO | WO 03086247 A1 | 10/2003 |
| WO | WO 03094785 A1 | 11/2003 |
| WO | WO 2004017863 A2 | 3/2004 |
| WO | WO 2004021894 A1 | 3/2004 |
| WO | WO 2004041119 A2 | 5/2004 |
| WO | WO 2004041133 A1 | 5/2004 |
| WO | WO 2004047686 A1 | 6/2004 |
| WO | WO 2004049982 A2 | 6/2004 |
| WO | WO 2004064680 A1 | 8/2004 |
| WO | WO 2004064685 A1 | 8/2004 |
| WO | WO 2004080336 A2 | 9/2004 |
| WO | WO 2004086984 A1 | 10/2004 |
| WO | WO 2004087014 A2 | 10/2004 |
| WO | WO 2004087233 A2 | 10/2004 |
| WO | WO 2004103214 A1 | 12/2004 |
| WO | WO 2004103430 A2 | 12/2004 |
| WO | WO 2004105643 A1 | 12/2004 |
| WO | WO 2005011463 A2 | 2/2005 |
| WO | WO 2005011519 A2 | 2/2005 |
| WO | WO 2005032422 A1 | 4/2005 |
| WO | WO 2005037152 A1 | 4/2005 |
| WO | WO 2005060869 A1 | 7/2005 |
| WO | WO 2005060882 A1 | 7/2005 |
| WO | WO 2005110280 A2 | 11/2005 |
| WO | WO 2006044640 A1 | 4/2006 |
| WO | WO 2006055847 A2 | 5/2006 |
| WO | WO 2006130836 A2 | 12/2006 |
| WO | WO 2007056583 A1 | 5/2007 |
| WO | WO 2008121409 A1 | 10/2008 |
| WO | WO 2009011881 A1 | 1/2009 |
| WO | WO 2011031981 A1 | 3/2011 |

OTHER PUBLICATIONS

Awan et al., Endoscopic vertical band gastroplasty with an endoscopic sewing machine, Gastrointestinal Endoscopy, vol. 55, No. 2, pp. 254-256, Feb. 2002.

Berger et al., Progression rate of self-propelled feeding tubes in critically ill patients, Intensive Care Medicine, vol. 28, No. 12, pp. 1768-1774, Dec. 2002.

Boston Scientific Corp., Website, Microvasive Wallstent® Colonic & Duodenal Endoprosthesis, Sep. 2002.

C.R. Bard, Inc., Website, The Bard EndoCinch Procedure, 2002.

Chuttani, Endoscopic full-thickness plication: the device, technique, pre-clinical and early clinical experience, Gastrointestinal Endoscopy Clinics of North America, vol. 13, No. 1, pp. 109-116, Jan. 2003.

Cook Inc., Brochure, Cope Gastrointestinal Suture Anchor Set, 2000.

Cook Inc., Website, Geenen® Pancreatic Stent Sets, Sep. 2002.

Crampton et al., Silastic Ring Gastric Bypass: Results in 64 Patients, Obesity Surgery, vol. 7, No. 6, pp. 489-494, Dec. 1997.

De La Fuente et al., Evaluation of porcine-derived small intestine submucosa as a biodegradable graft for gastrointestinal healing, Journal of Gastrointestinal Surgery (abstract), vol. 7, No. 1, pp. 96-101, Jan. 2003.

Demeester, Microvasive gastric stapler: the device, technique, and preclinical results, Gastrointestinal Endoscopy Clinics of North America, vol. 13, No. 1, pp. 117-133, Jan. 2003.

Espinet-Coll et al., Current endoscopic techniques in the treatment of obesity, Revista Española de Enfermedades Digestivas, vol. 104, No. 2, pp. 72-87, Feb. 2012.

Felsher et al., A Novel Endolaparoscopic Intragastric Partitioning for Treatment of Morbid Obesity, Surgical Laparoscopy, Endoscopy & Percutaneous Techniques, vol. 14, No. 5, pp. 243-246, Oct. 2004.

Fennerty, Endoscopic suturing for treatment of GERD, Gastrointestinal Endoscopy, vol. 57, No. 3, pp. 390-395, Mar. 2003.

Fobi et al., Gastric Bypass Operation for Obesity, World Journal of Surgery, vol. 22, No. 9, pp. 925-935, Sep. 1998.

Fritscher-Ravens et al., A through-the-scope device for suturing and tissue approximation under EUS control, Gastrointestinal Endoscopy, vol. 56, No. 5, pp. 737-742, Nov. 2002.

Fritscher-Ravens et al., Abstract, Endoscopic Gastropexy and Crural Repair for Gastro-Esophageal Reflux: Transgastric Surgery Under Endoscopic Ultrasound Control II, Gastroenterology, vol. 124, No. 4, supp. 1, p. A38, Apr. 2003.

Fritscher-Ravens et al., Transgastric gastropexy and hiatal hernia repair for GERD under EUS control: a porcine model, Gastrointestinal Endoscopy, vol. 59, No. 1, pp. 89-95, Jan. 2004.

Gleason, Bioabsorbable Polymers, 1998.

Godin et al., Abstract, Endoscopic suturing of a novel gastroesophageal antireflux device (GARD) a preliminary report, Gastrointestinal Endoscopy, vol. 43, No. 4, p. 336, Apr. 1996.

Kadirkamanathan et al., Antireflux operations at flexible endoscopy using endoluminal stitching techniques: an experimental study, Gastrointestinal Endoscopy, vol. 44, No. 2, pp. 133-143, Aug. 1996.

Keyser et al., Double Closed Loop Obstruction and Perforation in a Previous Roux-en-Y Gastric Bypass, Obesity Surgery, vol. 8, No. 4, pp. 475-479, Aug. 1998.

Kuo et al., Esophagus—anatomy and development, GI Motility online, Figure 8, 2006. http://www.nature.com/gimo/contents/pt1/full/gimo6.html#f8.

Long et al., Abstract, Techniques for advancing guide wires and devices in the lumen of the gastrointestinal tract, Gastrointestinal Endoscopy, vol. 57, No. 5, p. AB177, Apr. 2003.

Merlini et al., [Development of a gastroplasty with variable diameter. Experimental study using artificial sphincters] (abstract),

(56) References Cited

OTHER PUBLICATIONS

Helvetica Chirurgica Acta., vol. 58, No. 6, pp. 789-793, May 1992.
Middleton et al., Synthetic Biodegradable Polymers as Medical Devices, Medical Plastics and Biomaterials Magazine, Mar. 1998.
Mittal et al., Sphincter mechanisms at the lower end of the esophagus, GI Motility online, 2006. http://www.nature.com/gimo/contents/pt1/full/gimo14.html.
Nakamura et al., Experimental study on in situ tissue engineering of the stomach by an acellular collage sponge scaffold graft (abstract), ASAIO Journal, vol. 47, No. 3, pp. 206-210, May-Jun. 2001.
Oh et al., Weight Loss Following Transected Gastric Bypass with Proximal Roux-en-Y, Obesity Surgery, vol. 7, No. 2, pp. 142-147, Apr. 1997.
Oh et al., Repair of Full-Thickness Defects in Alimentary Tract Wall With Patches of Expanded Polytetrafluoroethylene, Annals of Surgery, vol. 235, No. 5, pp. 708-712, May 2002.
Paré Surgical, Inc., Brochure, Successful uses in approximation ligation & fixation using the Quik Stitch Endoscopic Suturing System, 2001.
Pories et al., Who Would Have Thought It? An Operation Proves to Be the Most Effective Therapy for Adult-Onset Diabetes Mellitus, Annals of Surgery, vol. 222, No. 3, pp. 339-352, Sep. 1995.
Redmond et al., Iatrogenic Intussusception: a Complication of Long Intestinal Tubes, American Journal of Gastroenterology, vol. 77, No. 1, pp. 39-42, Jan. 1982.
Rosen et al., Wilson-Cook sewing device: the device, technique, and preclinical studies, Gastrointestinal Endoscopy Clinics of North America, vol. 13, No. 1, pp. 103-108, Jan. 2003.
Rothstein et al., Endoscopic suturing for gastroesophageal reflux disease: clinical outcome with the Bard EndoCinch, Gastrointestinal Endoscopy Clinics of North America, vol. 13, No. 1, pp. 89-101, Jan. 2003.
Rubino et al., Effect of Duodenal-Jejunal Exclusion in a Non-obese Animal Model of Type 2 Diabetes, Annals of Surgery, vol. 239, No. 1, pp. 1-11, Jan. 2004.
Singh et al., Stents in the small intestine, Current Gastroenterology Reports (abstract), vol. 4, No. 5, pp. 383-391, Oct. 2002.
Stein et al., Three-dimensional pressure image and muscular structure of the human lower esophageal sphincter, Surgery, vol. 117, No. 6, pp. 692-698, Jun. 1995.
Sugermen et al., Weight Loss With Vertical Banded Gastroplasty and Roux-Y Gastric Bypass for Morbid Obesity With Selective Versus Random Assignment, The American Journal of Surgery, vol. 157, pp. 93-102, Jan. 1989.
Swain et al., An endoscopic stapling device: the development of a new flexible endoscopically controlled device for placing multiple transmural staples in gastrointestinal tissue, Gastrointestinal Endoscopy, vol. 35, No. 4, pp. 338-339, 1989.
Swain et al., Abstract, Design and testing of a new, small diameter, single stitch endoscopic sewing machine, Gastrointestinal Endoscopy, vol. 36, No. 2, pp. 213-214, Mar. 1990.
Swain et al., An endoscopically deliverable tissue-transfixing device for securing biosensors in the gastrointestinal tract, Gastrointestinal Endoscopy, vol. 40, No. 6, pp. 730-734, Nov. 1994.
Swain, Endoscopic suturing, Balliere's Clinical Gastroenterology, vol. 13, No. 1, pp. 97-108, 1999.
Swain et al., Bard EndoCinch: the device, the technique, and pre-clinical studies, Gastrointestinal Endoscopy Clinics of North America, vol. 13, No. 1, pp. 75-88, Jan. 2003.
Swain et al., Abstract, Radiocontrolled Movement of a Robot Endoscope in the Human Gastrointestinal Tract, Gastrointestinal Endoscopy, vol. 61, No. 5 , p. AB101, Apr. 2005.
Yamamoto et al., A new method of enteroscopy—The double-balloon method, Canadian Journal of Gastroenterology, vol. 17, No. 4, pp. 273-274, Apr. 2003.
U.S. Appl. No. 10/698,148, Aug. 8, 2006 non-final office action.
U.S. Appl. No. 10/698,148, Jul. 24, 2007 final office action.
U.S. Appl. No. 10/698,148, Mar. 18, 2008 non-final office action.
U.S. Appl. No. 10/698,148, Jul. 21, 2008 final office action.
U.S. Appl. No. 10/698,148, Feb. 19, 2009 non-final office action.
U.S. Appl. No. 10/698,148, Jul. 9, 2009 final office action.
U.S. Appl. No. 10/698,148, Nov. 12, 2010 examiner's answer.
U.S. Appl. No. 10/698,148, Feb. 21, 2013 patent board decision.
U.S. Appl. No. 10/698,148, Jun. 6, 2013 non-final office action.
U.S. Appl. No. 10/698,148, Dec. 18, 2013 final office action.
U.S. Appl. No. 10/698,148, Feb. 18, 2015 notice of allowance.
EP patent application EP 03781672, Aug. 29, 2007 communication.
EP patent application EP 03781672, Jan. 9, 2009 communication.
PCT application PCT/US2003/034822, Apr. 2, 2004 ISR.
U.S. Appl. No. 10/998,424, Jun. 9, 2010 non-final office action.
U.S. Appl. No. 10/998,424, Nov. 24, 2010 final office action.
U.S. Appl. No. 14/738,597, Nov. 6, 2015 non-final office action.
U.S. Appl. No. 14/738,597, Sep. 21, 2016 notice of allowance.
U.S. Appl. No. 11/025,364, Nov. 17, 2006 non-final office action.
U.S. Appl. No. 11/025,364, Jan. 3, 2008 final office action.
U.S. Appl. No. 11/025,364, Feb. 12, 2009 non-final office action.
U.S. Appl. No. 11/025,364, Nov. 16, 2009 non-final office action.
U.S. Appl. No. 11/025,364, Aug. 6, 2010 final office action.
EP patent application EP 04816031, Sep. 22, 2008 supplemental search.
EP patent application EP 04816031, Feb. 19, 2009 communication.
EP patent application EP 04816031, Jun. 11, 2010 communication.
PCT application PCT/US2004/044049, May 30, 2007 ISR/WO.
U.S. Appl. No. 11/124,634, May 13, 2010 non-final office action.
U.S. Appl. No. 11/124,634, Nov. 30, 2010 final office action.
U.S. Appl. No. 11/124,634, Sep. 23, 2011 notice of allowance.
EP patent application EP 05747626, Sep. 18, 2008 supplemental search.
EP patent application EP 05747626, Aug. 25, 2009 communication.
EP patent application EP 05747626, Nov. 15, 2011 communication.
PCT application PCT/US2005/015795, Nov. 14, 2005 ISR/WO.
U.S. Appl. No. 11/400,724, Oct. 10, 2007 non-final office action.
U.S. Appl. No. 11/400,724, Mar. 24, 2008 final office action.
U.S. Appl. No. 11/400,724, Dec. 15, 2008 non-final office action.
U.S. Appl. No. 11/400,724, Jul. 7, 2009 non-final office action.
U.S. Appl. No. 11/400,724, Sep. 20, 2010 notice of allowance.
U.S. Appl. No. 11/548,605, Nov. 9, 2010 non-final office action.
U.S. Appl. No. 11/548,605, May 24, 2011 final office action.
U.S. Appl. No. 11/548,605, Mar. 15, 2012 notice of allowance.
EP patent application EP 07809011, Jun. 10, 2014 supplemental search.
PCT application PCT/US2007/008882, Dec. 26, 2007 ISR/WO.
U.S. Appl. No. 13/373,999, Jul. 9, 2012 non-final office action.
U.S. Appl. No. 13/373,999, May 24, 2013 final office action.
U.S. Appl. No. 13/373,999, Oct. 21, 2014 notice of allowance.
U.S. Appl. No. 14/634,548, Jul. 15, 2015 non-final office action.
U.S. Appl. No. 14/634,548, Jun. 15, 2016 final office action.
U.S. Appl. No. 13/476,884, Apr. 9, 2013 non-final office action.
U.S. Appl. No. 13/476,884, Dec. 24, 2013 non-final office action.
U.S. Appl. No. 13/476,884, Mar. 20, 2015 non-final office action.
U.S. Appl. No. 13/476,884, Jul. 20, 2015 final office action.
U.S. Appl. No. 13/476,884, Oct. 3, 2016 examiner's answer.
U.S. Appl. No. 11/431,040, Oct. 15, 2010 non-final office action.
U.S. Appl. No. 11/431,040, Jun. 21, 2011 notice of allowance.
U.S. Appl. No. 11/430,677, Apr. 2, 2009 non-final office action.
U.S. Appl. No. 11/430,677, Jan. 11, 2010 final office action.
U.S. Appl. No. 11/430,677, Sep. 23, 2010 notice of allowance.
U.S. Appl. No. 11/431,054, Oct. 27, 2010 non-final office action.
U.S. Appl. No. 11/430,275, Oct. 9, 2007 non-final office action.
U.S. Appl. No. 11/430,275, Sep. 16, 2008 final office action.
U.S. Appl. No. 11/430,275, Dec. 29, 2008 non-final office action.
U.S. Appl. No. 11/430,275, Jul. 21, 2009 final office action.
U.S. Appl. No. 11/430,275, Oct. 19, 2010 non-final office action.
U.S. Appl. No. 11/430,278, Jul. 3, 2007 non-final office action.
U.S. Appl. No. 11/430,278, Mar. 25, 2008 final office action.
U.S. Appl. No. 11/430,278, Jun. 4, 2008 non-final office action.
U.S. Appl. No. 11/430,278, Dec. 16, 2008 final office action.
U.S. Appl. No. 11/430,278, Oct. 20, 2009 non-final office action.
U.S. Appl. No. 11/430,278, Jul. 22, 2010 final office action.
U.S. Appl. No. 11/430,278, Jun. 20, 2011 notice of allowance.
U.S. Appl. No. 11/430,274, Oct. 5, 2009 non-final office action.
U.S. Appl. No. 11/430,274, May 11, 2010 final office action.
U.S. Appl. No. 11/430,274, Sep. 30, 2010 notice of allowance.

(56) References Cited

OTHER PUBLICATIONS

U.S. Appl. No. 11/429,934, May 26, 2010 non-final office action.
U.S. Appl. No. 11/429,934, Feb. 17, 2011 final office action.
U.S. Appl. No. 10/699,589, Dec. 13, 2004 non-final office action.
U.S. Appl. No. 10/699,589, Jun. 6, 2005 final office action.
U.S. Appl. No. 10/903,255, Aug. 23, 2006 non-final office action.
U.S. Appl. No. 10/903,255, Apr. 18, 2007 non-final office action.
U.S. Appl. No. 10/903,255, Sep. 24, 2007 final office action.
U.S. Appl. No. 10/903,255, Jan. 10, 2008 non-final office action.
U.S. Appl. No. 10/903,255, Nov. 14, 2008 final office action.
U.S. Appl. No. 10/903,255, Oct. 30, 2009 non-final office action.
U.S. Appl. No. 10/903,255, Feb. 22, 2010 non-final office action.
U.S. Appl. No. 10/903,255, Jun. 8, 2010 final office action.
U.S. Appl. No. 10/903,255, Jul. 27, 2010 notice of allowance.
U.S. Appl. No. 11/169,341, Dec. 13, 2006 non-final office action.
U.S. Appl. No. 11/236,212, Mar. 18, 2008 non-final office action.
U.S. Appl. No. 11/236,212, Oct. 7, 2009 final office action.
U.S. Appl. No. 11/236,212, Apr. 26, 2010 non-final office action.
U.S. Appl. No. 11/236,212, May 4, 2011 final office action.
U.S. Appl. No. 13/289,885, Aug. 15, 2012 non-final office action.
U.S. Appl. No. 11/123,889, May 24, 2010 non-final office action.
U.S. Appl. No. 11/123,889, Feb. 2, 2011 final office action.
U.S. Appl. No. 13/196,812, Jun. 18, 2012 non-final office action.
U.S. Appl. No. 13/196,812, Feb. 7, 2013 final office action.
U.S. Appl. No. 13/196,812, Oct. 17, 2013 non-final office action.
U.S. Appl. No. 13/196,812, May 5, 2014 final office action.
U.S. Appl. No. 11/125,820, May 30, 2008 non-final office action.
U.S. Appl. No. 11/125,820, Aug. 14, 2009 final office action.
U.S. Appl. No. 11/125,820, Feb. 4, 2010 non-final office action.
U.S. Appl. No. 11/125,820, Oct. 15, 2010 final office action.
U.S. Appl. No. 11/789,561, Mar. 29, 2010 non-final office action.
U.S. Appl. No. 11/789,561, Nov. 16, 2010 notice of allowance.
PCT application PCT/US2007/009956, Dec. 28, 2007 ISR/WO.
U.S. Appl. No. 13/018,179, Aug. 2, 2012 non-final office action.
U.S. Appl. No. 13/018,179, Mar. 12, 2013 final office action.
U.S. Appl. No. 13/018,179, Apr. 23, 2014 non-final office action.
U.S. Appl. No. 11/861,172, Nov. 10, 2008 non-final office action.
U.S. Appl. No. 11/861,172, Jul. 14, 2009 final office action.
U.S. Appl. No. 11/861,172, May 21, 2013 non-final office action.
U.S. Appl. No. 11/861,172, Apr. 11, 2014 notice of allowance.
U.S. Appl. No. 14/461,774, Apr. 17, 2015 final office action.
U.S. Appl. No. 14/461,774, Sep. 21, 2015 non-final office action.
U.S. Appl. No. 14/461,774, Apr. 29, 2016 final office action.
U.S. Appl. No. 11/861,156, Jun. 2, 2009 non-final office action.
U.S. Appl. No. 11/861,156, Dec. 31, 2009 final office action.
U.S. Appl. No. 11/861,156, Sep. 22, 2010 non-final office action.
U.S. Appl. No. 11/861,156, Jun. 23, 2011 final office action.
U.S. Appl. No. 11/861,156, Oct. 11, 2011 notice of allowance.
EP patent application EP 07843175, Oct. 1, 2013 supplemental search.
EP patent application EP 07843175, Jun. 11, 2014 communication.
PCT application PCT/US2007/079460, May 19, 2008 ISR/WO.
U.S. Appl. No. 12/136,003, Sep. 27, 2010 non-final office action.
U.S. Appl. No. 12/136,003, May 10, 2011 final office action.
U.S. Appl. No. 12/136,003, Mar. 13, 2012 notice of allowance.
EP patent application EP 08770415, Jul. 7, 2010 supplemental search.
PCT application PCT/US2008/066214, Oct. 1, 2008 ISR/WO.
U.S. Appl. No. 13/476,837, Oct. 14, 2014 non-final office action.
U.S. Appl. No. 12/135,989, Sep. 16, 2010 non-final office action.
U.S. Appl. No. 12/135,989, May 25, 2011 final office action.
U.S. Appl. No. 12/137,473, Sep. 29, 2010 non-final office action.
U.S. Appl. No. 12/137,473, May 31, 2011 final office action.
U.S. Appl. No. 12/137,473, Dec. 2, 2013 non-final office action.
U.S. Appl. No. 12/137,473, Jun. 25, 2014 final office action.
U.S. Appl. No. 12/137,473, Jan. 28, 2015 non-final office action.
EP patent application EP 08770736, May 23, 2011 supplemental search.
EP patent application EP 08770736, Mar. 23, 2015 communication.
PCT application PCT/US2008/066590, Dec. 5, 2008 ISR/WO.
U.S. Appl. No. 13/485,887, Aug. 6, 2013 non-final office action.
U.S. Appl. No. 13/485,887, Mar. 17, 2014 final office action.
U.S. Appl. No. 13/485,887, Oct. 2, 2014 notice of allowance.
U.S. Appl. No. 13/485,889, Aug. 8, 2013 non-final office action.
U.S. Appl. No. 13/485,893, Aug. 23, 2013 non-final office action.
U.S. Appl. No. 13/485,896, Mar. 5, 2015 non-final office action.
U.S. Appl. No. 13/485,896, Jul. 28, 2015 final office action.
U.S. Appl. No. 13/485,896, Apr. 26, 2016 notice of allowance.
U.S. Appl. No. 13/485,898, Jul. 3, 2013 non-final office action.
U.S. Appl. No. 13/485,898, Feb. 14, 2014 final office action.
U.S. Appl. No. 13/485,898, Jun. 6, 2014 non-final office action.
U.S. Appl. No. 13/485,898, Dec. 29, 2014 final office action.
U.S. Appl. No. 13/485,898, Jun. 18, 2015 notice of allowance.
U.S. Appl. No. 13/743,285, Mar. 20, 2015 non-final office action.
U.S. Appl. No. 13/743,287, Mar. 23, 2015 non-final office action.
U.S. Appl. No. 13/743,287, Jul. 9, 2015 final office action.
U.S. Appl. No. 13/896,838, Apr. 10, 2015 non-final office action.
U.S. Appl. No. 13/896,838, Sep. 2, 2015 final office action.
U.S. Appl. No. 13/896,838, Apr. 11, 2016 non-final office action.
U.S. Appl. No. 13/896,838, Nov. 15, 2016 notice of allowance.
EP patent application EP 13796584, Feb. 18, 2016 communication.
PCT application PCT/US2013/043741, Dec. 2, 2013 ISR/WO.
U.S. Appl. No. 14/315,330, Feb. 12, 2016 non-final office action.
U.S. Appl. No. 14/139,859, Jul. 17, 2015 non-final office action.
U.S. Appl. No. 15/000,959, Oct. 6, 2016 non-final office action.
U.S. Appl. No. 14/164,112, Jan. 14, 2016 non-final office action.
PCT application PCT/US2014/013069, Apr. 17, 2014 ISR/WO.
PCT application PCT/US2015/058690, Mar. 17, 2016 ISR/WO.
PCT application PCT/US2015/058691, Jan. 27, 2016 ISR/WO.

* cited by examiner

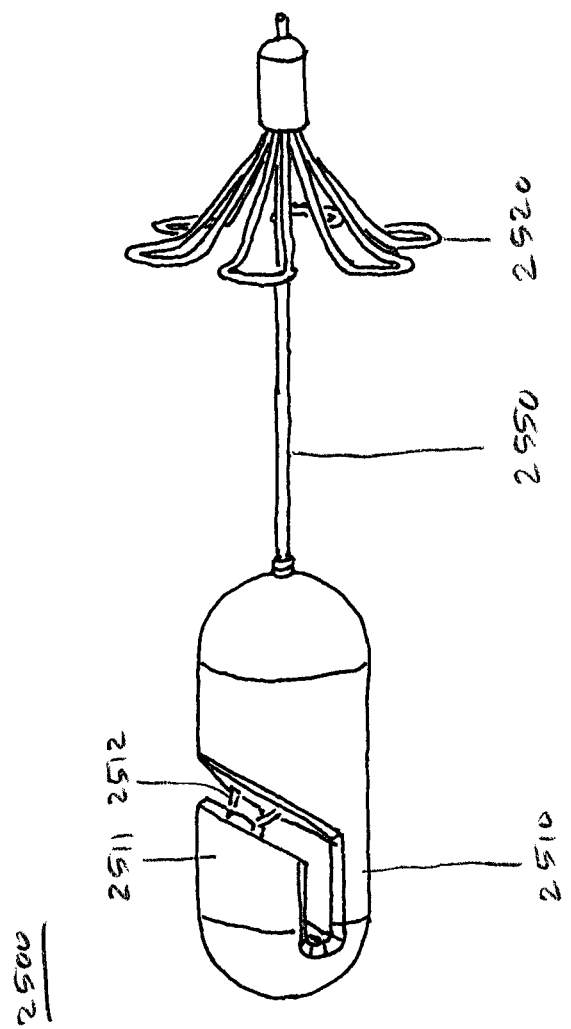

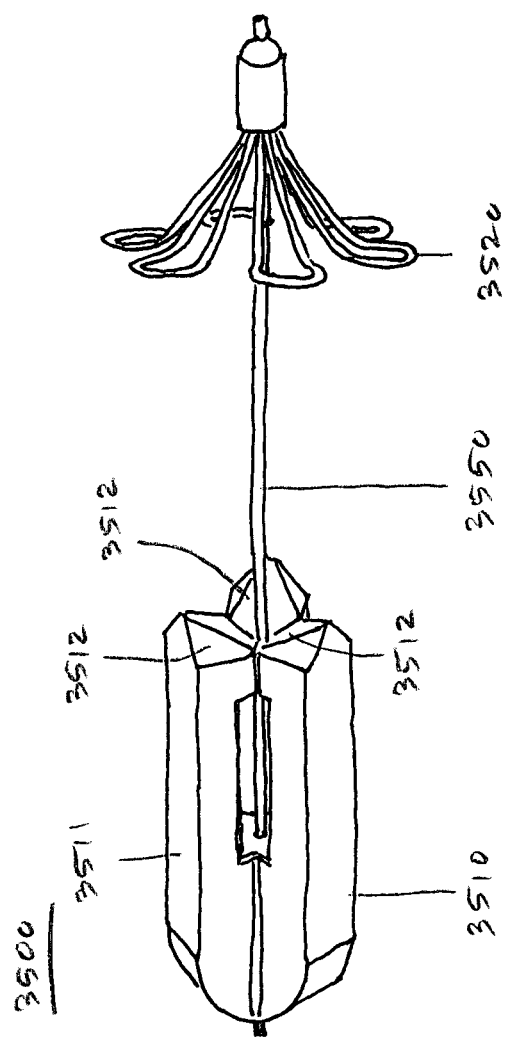

DEVICES AND METHODS FOR GASTROINTESTINAL BYPASS

CROSS-REFERENCE TO RELATED APPLICATION

This application claims the benefit of U.S. provisional patent application Ser. No. 61/780,777, filed Mar. 13, 2013, which is hereby incorporated by reference in its entirety.

BACKGROUND

Diabetes, heart disease, and other obesity-related conditions may be treated surgically with bariatric procedures such as jejuno-ileal bypass, jejuno-colic bypass, biliopancreatic diversion, gastric bypass, and gastroplasty. These procedures may be effective for weight control and treatment of chronic conditions. However, these procedures carry with them substantial shortcomings, including the risk of infection and other risks accompanying surgery. Some of these procedures effect radical permanent changes to the gastrointestinal anatomy, thus foreclosing subsequent surgical intervention.

What is needed are devices and methods for gastrointestinal bypass that avoid the risks associated with surgery by using non-surgical techniques. What is also needed are devices and methods for gastrointestinal bypass that allow for additional or revision procedures to be performed. What is also needed are devices and methods for gastrointestinal bypass that are reversible.

SUMMARY

A gastrointestinal bypass device for directing food and liquids from an esophagus and/or a proximal portion of a stomach into an intestines is described. The device comprises a receiver, a sleeve, and a device coupling.

The receiver may be configured to be positioned in the esophagus and/or the stomach. A proximal portion of the receiver may be configured to open and close to at least partially conform to an inside of the esophagus and/or a proximal portion of the stomach. The receiver may be configured to receive food and liquids from the esophagus and/or a proximal portion of the stomach into a lumen of the receiver.

The sleeve may be coupled to a distal portion of the receiver. The sleeve may be configured to be positioned in the stomach and the intestines. The sleeve may have a lumen in communication with the lumen of the receiver. The sleeve may be configured to direct the food and the liquids from the receiver into the intestines.

The device coupling may be coupled to the distal portion of the receiver and/or a proximal portion of the sleeve. The device coupling may be configured to be coupled to one or more tissue anchors.

BRIEF DESCRIPTION OF THE DRAWINGS

FIGS. 3F-3G show perspective and side views, respectively, of one embodiment of a tissue anchor 2500.

FIG. 5C shows one embodiment of a tissue anchor 3500.

DESCRIPTION

Figure 1A:
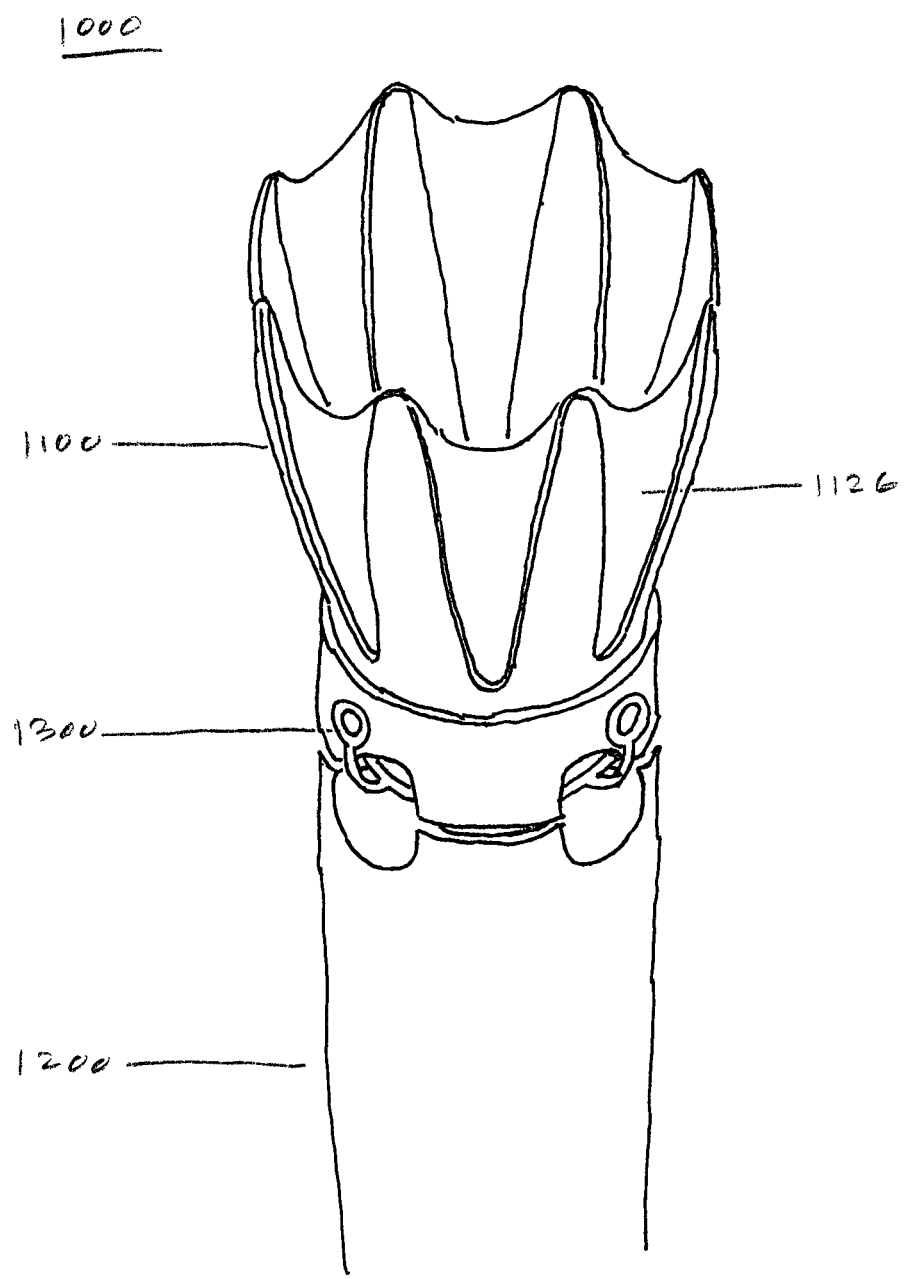
FIGS. 1A-1D show perspective, exploded, side, and cross-sectional views, respectively, of one embodiment of gastrointestinal bypass device 1000.
Figure 1B:
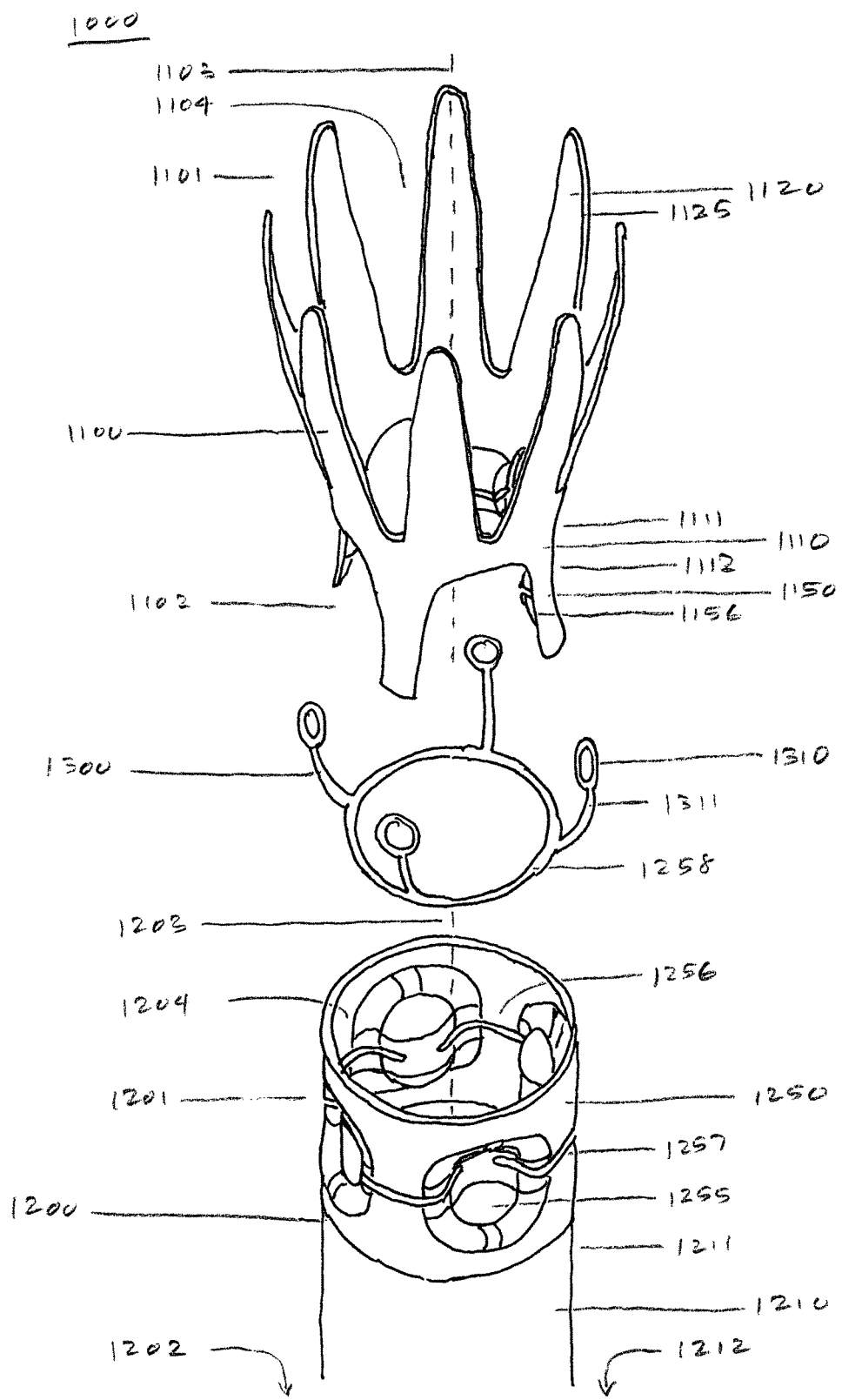
Figure 1C:
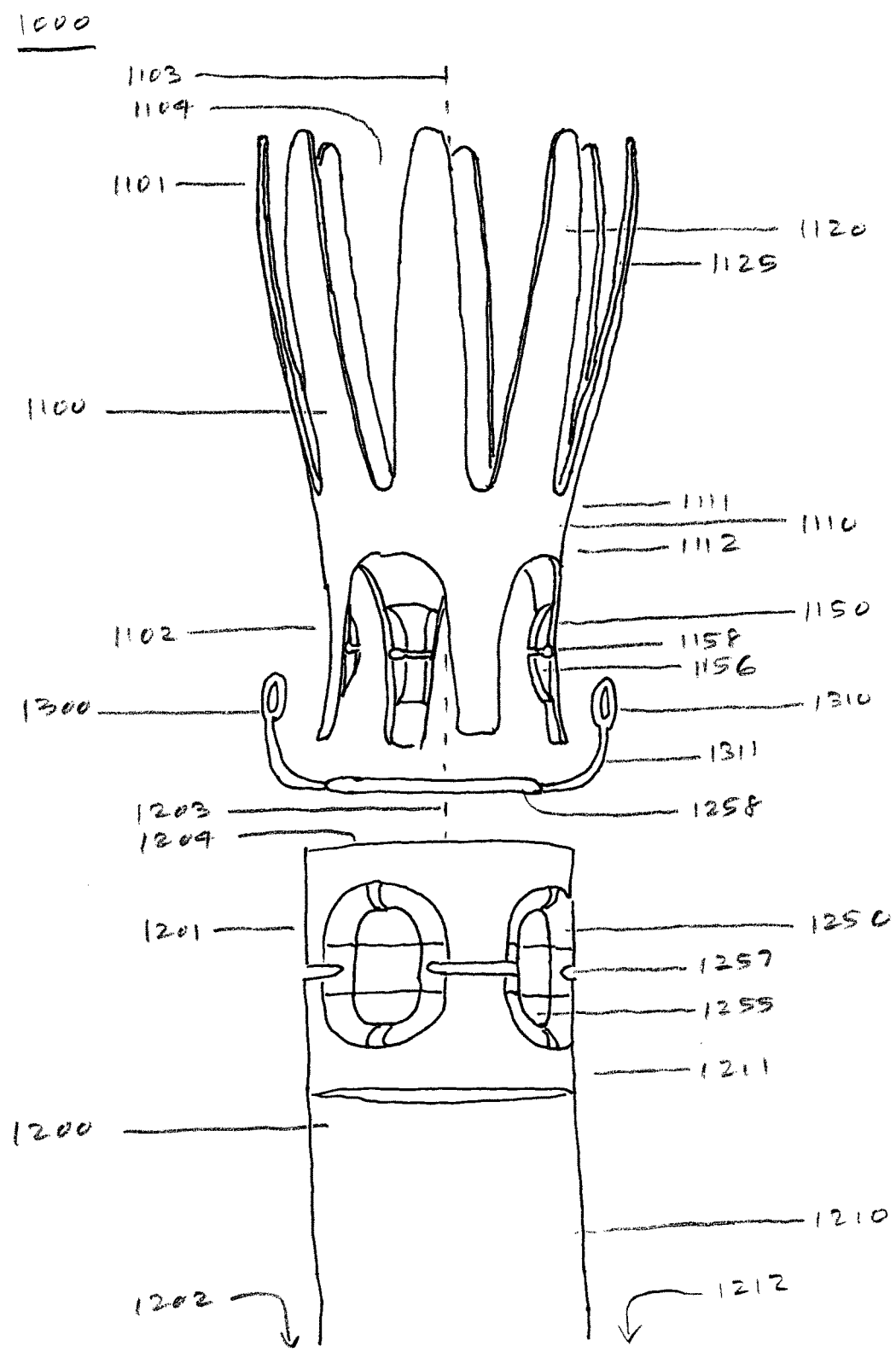
Figure 1D:
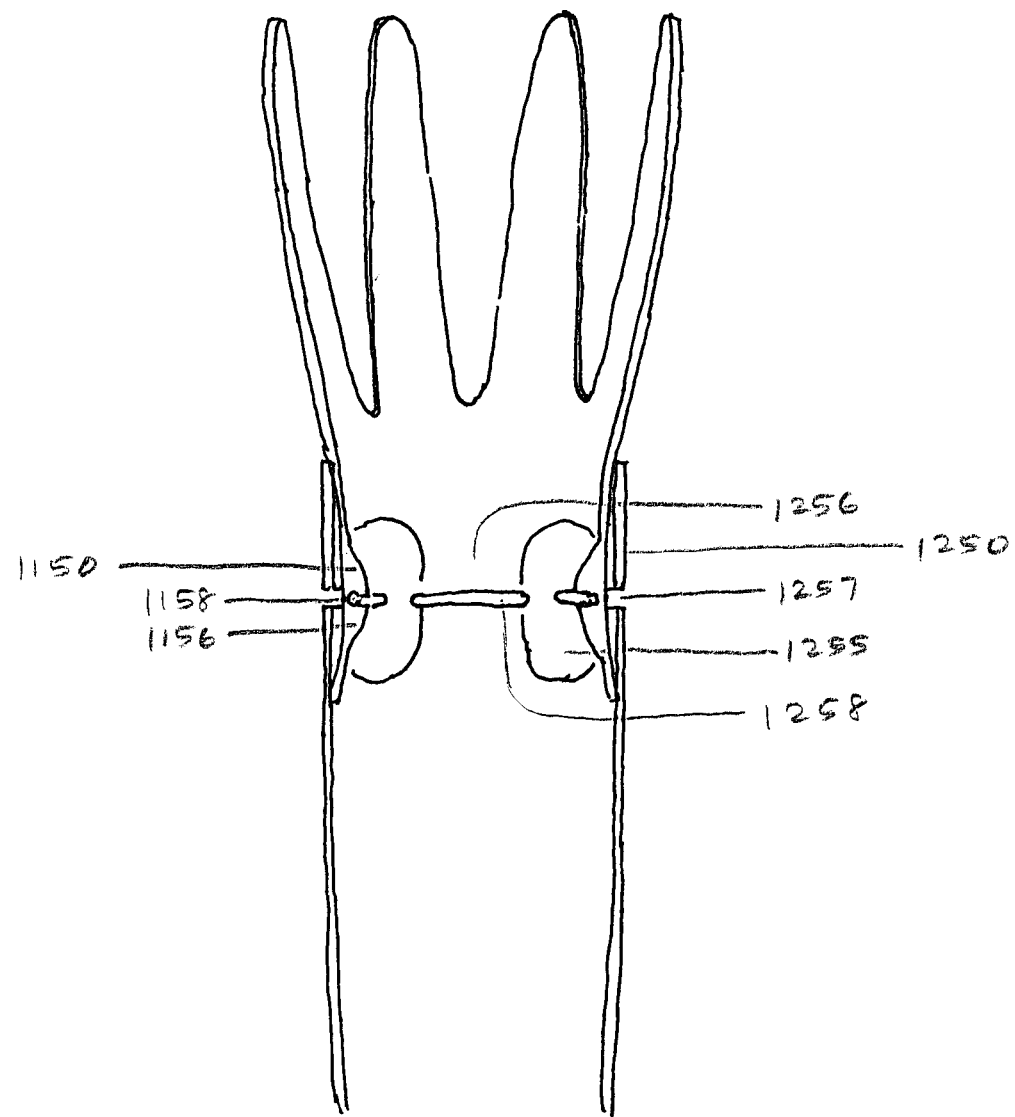

FIGS. 1A-1D show perspective, exploded, side, and cross-sectional views, respectively, of one embodiment of gastrointestinal bypass device 1000.

Gastrointestinal bypass device 1000 may be used for directing food and liquids from the esophagus and/or a proximal portion of the stomach into the intestines.

Gastrointestinal bypass device 1000 may include a receiver 1100, a sleeve 1200, and a device coupling 1300. Gastrointestinal bypass device 1000 may be configured to be used with one or more tissue anchors 1500.

Receiver 1100 may include a proximal portion 1101, a distal portion 1102, a longitudinal axis 1103, and a lumen 1104. Receiver 1100 may be configured to be positioned in the esophagus and/or the stomach. Receiver 1100 may be configured to receive food and liquids from the esophagus and/or a proximal portion of the stomach into lumen 1104. Receiver 1100 may be configured to reduce the amount of food and liquids which pass to an outside of receiver 1100 instead of through lumen 1104. Proximal portion 1101 of receiver 1100 may be configured to open and close to at least partially conform to an inside of the esophagus and/or a proximal portion of the stomach.

Receiver 1100 may include a body 1110, a plurality of fingers 1120, and a receiver coupling 1150.

Body 1110 may include a proximal portion 1111 and a distal portion 1112. Body 1110 may be configured to be positioned in the esophagus and/or the stomach. Body 1110 may be configured to be positioned distal to the lower esophageal sphincter. Body 1110 may provide support to fingers 1120. Body 1110 may include a ring or a short tubular element. Body 1110 may be flexible. Body 1110 may have sufficient hoop strength to resist radial expansion. Body 1110 may be made of a polyurethane elastomer such as PELLETHANE, silicone, and/or any other suitable material.

Fingers 1120 may extend proximally from proximal portion 1111 of body 1110. Fingers 1120 may be configured to extend into a proximal portion of the stomach, at least partially through the lower esophageal sphincter, above the lower esophageal sphincter, or anywhere in the esophagus. Fingers 1120 may be configured to open and close to at least partially conform to an inside of the esophagus and/or a proximal portion of the stomach. Fingers 1120 may be configured to have an outward bias that is large enough to at least partially conform to an inside of the esophagus and/or a proximal portion of the stomach. Fingers 1120 may be configured to have an outward bias that is small enough not to substantially interfere with the closing or normal functioning of the esophagus and/or a proximal portion of the stomach. Fingers 1120 may use body 1110 as a fulcrum to maintain at least a portion of an outward bias.

Fingers 1120 may have a shape that cooperates with other fingers 1120 when fingers 1120 are closed. Fingers 1120 may have a shape that is sinusoidal, triangular, or any other suitable shape. Fingers 1120 may have a cross section that is flat, cylindrical, or any other suitable cross section. Fingers 1120 may have a uniform or varying thickness. Fingers 1120 may be flexible. Fingers 1120 may be made of a polyurethane elastomer such as PELLETHANE, silicone, and/or any other suitable material.

Fingers 1120 may include one or more stiffening elements 1125 coupled around the edge of fingers 1120. Alternatively, stiffening elements 1125 may be coupled along the center of fingers 1120 and/or any other suitable location. Stiffening elements 1125 may provide at least some support to fingers 1120 to extend proximally. Stiffening elements 1125 may provide at least some outward bias to fingers 1120 to conform to an inside of the esophagus and/or a proximal portion of the stomach. Stiffening elements 1125 may reduce the likelihood of fingers 1120 being inverted distally into lumen 1114, or help allow inverted fingers 1120 to reposition themselves. Stiffening elements 1125 may include a wire, stent, scaffold, thickened portions of fingers 1120, and/or any other suitable element. Stiffening elements 1125 may be made of a metal, plastic, and/or any other suitable material.

Alternatively, stiffening elements 1125 may be similar in part or in whole to one or more of the scaffolds and/or struts described in U.S. patent application Ser. No. 13/485,887 (VALENTX 021A1), which is hereby incorporated by reference in its entirety.

Fingers 1120 may include webbing 1126 coupled between fingers 1120. Webbing 1126 may cover a portion or substantially all of the space between adjacent fingers 1120. Webbing 1126 may reduce the amount of food and liquids leaking out between fingers 1120. Webbing 1126 may be flexible. Webbing 1126 may be stretchable or non-stretchable. Webbing 1126 may be sufficiently thin to reduce bunching when fingers 1120 close. Webbing 1126 may be made of a polyurethane elastomer such as PELLETHANE, silicone, and/or any other suitable material. For clarity, webbing 1126 is not shown in FIGS. 1B-1D.

Receiver coupling 1150 may be coupled to body 1110. Receiver coupling 1150 may be configured to be removably or irremovably coupled to sleeve 1200. Receiver coupling 1150 may include one or more clips 1156. Clips 1156 may extend distally from distal portion 1112 of body 1110. Clips 1156 may include channels 1158. Alternatively, receiver coupling 1150 may include a hook, loop, retainer, or any other suitable device.

Alternatively, receiver coupling 1150 may be similar in part or in whole to those described in U.S. patent application Ser. No. 13/485,887 (VALENTX 021A1), which is hereby incorporated by reference in its entirety.

Alternatively, receiver 1100 may be any suitably shaped structure, such as a bowl-, cup-, or cone-shaped structure, having a proximal portion configured to open and close to conform to an inside of the esophagus and/or a proximal portion of the stomach, without substantially interfering with the closing or normal functioning of the esophagus and/or a proximal portion of the stomach.

Sleeve 1200 may include a proximal portion 1201, a distal portion 1202, a longitudinal axis 1203, and a lumen 1204. Sleeve 1200 may be coupled to distal portion 1102 of receiver 1100. Sleeve 1200 may be configured to be positioned in the stomach and the intestines. Lumen 1204 of sleeve 1200 may be in communication with lumen 1104 of receiver 1100. Sleeve 1200 may be configured to direct food and liquids from receiver 1100 into the intestines.

Sleeve 1200 may include a tube 1210 and a sleeve coupling 1250. Tube 1210 may include a proximal portion 1211 and a distal portion 1212. Tube 1210 may be similar in part or in whole to one or more of the tubes described in U.S. patent application Ser. No. 13/485,887 (VALENTX 021A1), which is hereby incorporated by reference in its entirety.

Sleeve coupling 1250 may be coupled to proximal portion 1211 of tube 1210. Sleeve coupling 1250 may be configured to be coupled to receiver coupling 1150 of receiver 1100. Sleeve coupling 1250 may include a portion of proximal portion 1211 of tube 1210. Sleeve coupling 1250 may be made of a similar or different material than tube 1210. Sleeve coupling 1250 may be of the same or different thickness than tube 1210.

Sleeve coupling 1250 may include a plurality of dimples 1255, a plurality of slots 1257, and a ring 1258. Dimples 1255 may be formed circumferentially around sleeve coupling 1250. Dimples 1255 may extend inwardly. Dimples 1255 may define spaces 1256 between adjacent dimples 1255. Spaces 1256 may be configured to receive clips 1156. Slots 1257 may be formed circumferentially around sleeve coupling 1250. Slots 1257 may extend across spaces 1256. Slots 1257 may also extend partially into dimples 1255. Slots 1257 may be configured to be coupled to ring 1258. Ring 1258 may be positioned to pass through slots 1257 and pass through spaces 1256. Ring 1258 may be made of suture, wire, and/or any other suitable material. Ring 1258 may be configured to be removably or irremovably coupled to channels 1158 of clips 1156. Alternatively, sleeve coupling 1250 may include a hook, loop, retainer, or any other suitable device.

Alternatively, sleeve coupling 1250 may be similar in part or in whole to those described in U.S. patent application Ser. No. 13/485,887 (VALENTX 021A1), which is hereby incorporated by reference in its entirety.

Device coupling 1300 may be coupled to ring 1258. Alternatively, device coupling 1300 may be coupled to distal portion 1102 of receiver 1100 and/or proximal portion 1201 of sleeve 1200. Device coupling 1300 may thus be distanced from proximal portion 1101 of receiver 1100. Distancing device coupling 1300 from proximal portion 1101 of receiver 1100 serves to separate the function of coupling to tissue anchors 1500 and the function of conforming to the inside of the esophagus and/or proximal portion of the stomach. This also allows the option of delivering tissue anchors 1500 below the lower esophageal sphincter while having receiver 1100 extend into or proximal to the lower esophageal sphincter. This also allows for greater variation in the lengths of the tension element in the tissue anchors.

Device coupling 1300 may be configured to be removably or irremovably coupled to tissue anchors 1500. Device coupling 1300 may include one or more loops 1310. Loops 1310 may be coupled to ring 1258. Loops 1310 may be rigid or flexible. Loops 1310 may be coupled with a plurality of standoffs 1311. Alternatively, loops 1310 may be coupled to distal portion 1102 of receiver 1100 and/or proximal portion 1201 of sleeve 1200.

Alternatively, device coupling 1300 may be similar in part or in whole to one or more of the device couplings described in U.S. provisional patent application Ser. No. 61/756,366 (VALENTX 024), which is hereby incorporated by reference in its entirety.

One or more elements of gastrointestinal bypass device 1000 may be formed integrally as a single piece, using one or more materials. For example, receiver 1100, sleeve 1200, and device coupling 1200 may be formed integrally as a single piece. As another example, receiver 1100 and sleeve 1200 may be formed integrally as a single piece, with the exception of webbing 1126 between fingers 1120, which may be added on later.

Figure 1E:
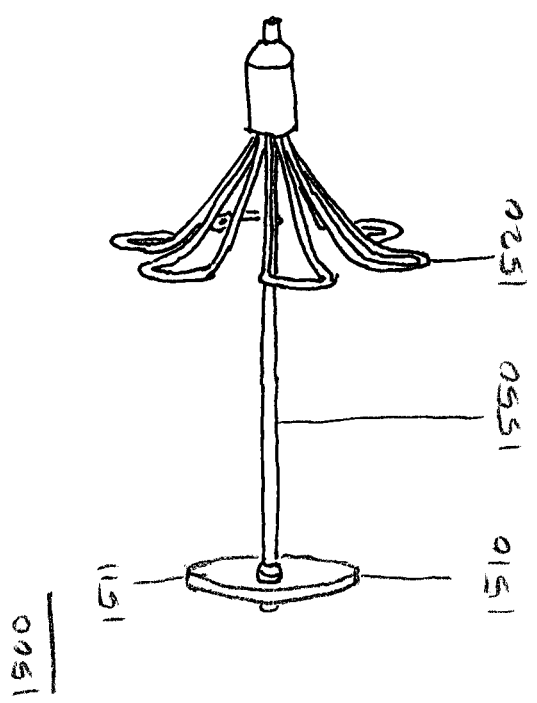
FIG. 1E shows one embodiment of a tissue anchor 1500.

FIG. 1E shows one embodiment of a tissue anchor 1500. Tissue anchor 1500 may include an anchor coupling 1510, a distal retention element 1520, and a tension element 1550.

Anchor coupling 1510 may be configured to be coupled to device coupling 1300. Anchor coupling 1510 may include a button 1511. Button 1511 may be sized larger than loop 1310.

Distal retention element 1520 may be configured to be deployed outside of a wall of the esophagus and/or a proximal portion of the stomach. Distal retention element 1520 may be similar in part or in whole to one or more of the distal retention elements described in the following, which are hereby incorporated by reference in their entireties: U.S. Pat. No. 8,070,743 (VALTX.001CP2); U.S. patent application Ser. No. 12/137,473 (VALTX.020A), Ser. No. 13/485,887 (VALENTX 021A1), and Ser. No. 13/743,287 (VALENTX 021CP2); U.S. provisional patent application Ser. No. 61/756,366 (VALENTX 024).

Tension element 1550 may include a proximal portion 1551 and a distal portion 1552. Proximal portion 1551 of tension element 1550 may be fixedly or adjustably coupled to anchor coupling 1510. Distal portion 1552 of tension element 1550 may be fixedly or adjustably coupled to distal retention element 1520. Tension element 1550 may be configured to pass through a wall of the esophagus and/or a proximal portion of the stomach.

Alternatively, tissue anchor 1500 may be similar in part or in whole to one or more of the tissue anchors described in the following, which are hereby incorporated by reference in their entireties: U.S. Pat. No. 8,070,743 (VALTX.001CP2); U.S. patent application Ser. No. 12/137,473 (VALTX.020A), Ser. No. 13/485,887 (VALENTX 021A1), and Ser. No. 13/743,287 (VALENTX 021CP2); U.S. provisional patent application Ser. No. 61/756,366 (VALENTX 024).

FIGS. 2A-2D show one embodiment of method for delivering gastrointestinal bypass device 1000. Sleeve 1200 may first be loaded onto a sleeve delivery device.

The sleeve delivery device may be similar in part or in whole to one or more of the sleeve delivery devices described in U.S. patent application Ser. No. 13/485,887 (VALENTX 021A1), which is hereby incorporated by reference in its entirety.

Figure 2A:
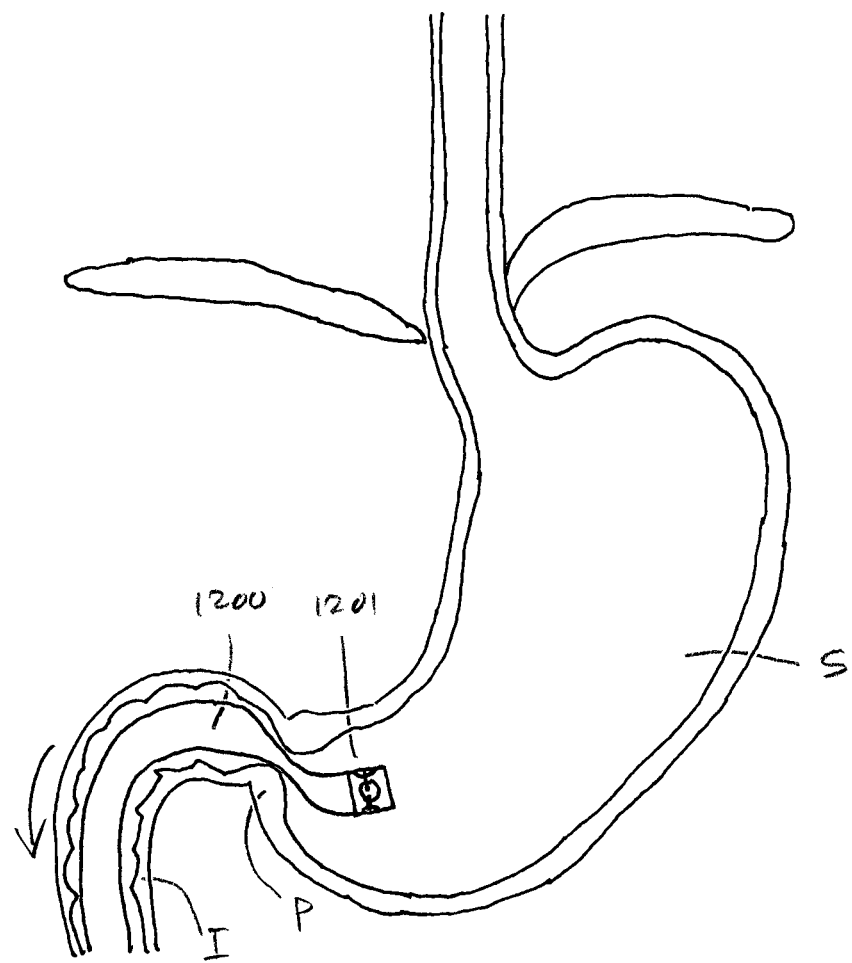
FIGS. 2A-2D show one embodiment of method for delivering gastrointestinal bypass device 1000.

FIG. 2A shows positioning proximal portion 1201 of sleeve 1200 at or near the pylorus P. Sleeve 1200 is then deployed into the intestines I.

The anchor site may first be marked using a tissue marking device before tissue anchors 1500 are delivered to aid in placement of tissue anchors 1500. The tissue marking device may be similar in part or in whole to one or more of the tissue marking devices described in U.S. patent application Ser. No. 13/485,887 (VALENTX 021A1), which is hereby incorporated by reference in its entirety.

Figure 2B:
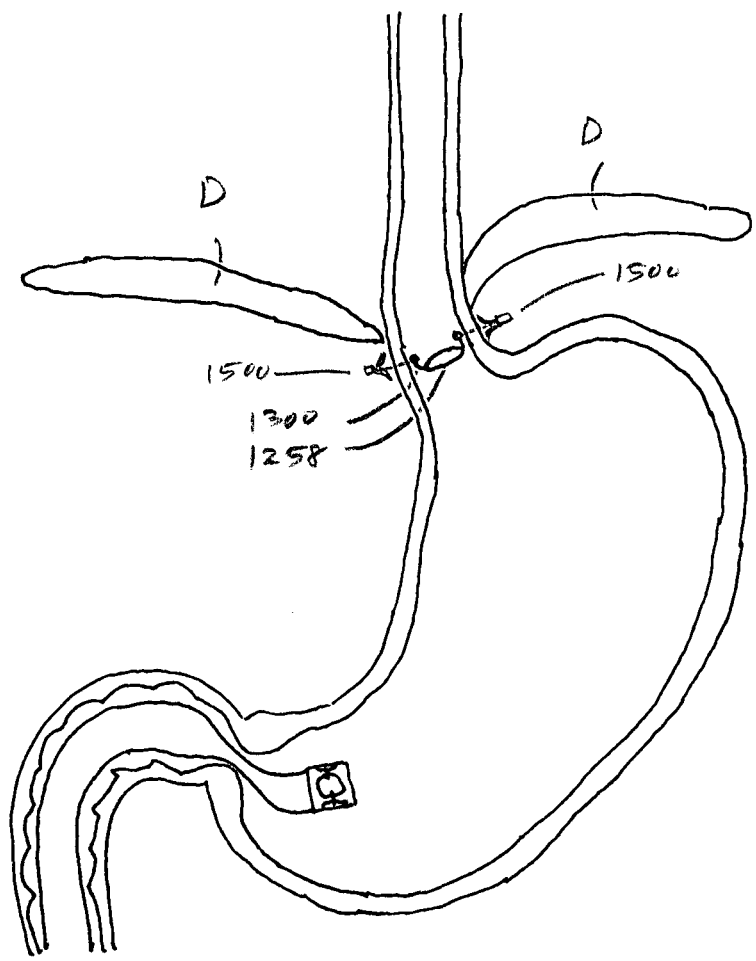

FIG. 2B shows delivering tissue anchors 1500 through loops 1310 of device coupling 1300 and through the wall of the esophagus E and/or a proximal portion of the stomach S at the anchor site. Alternatively, tissue anchors 1500 may be delivered first before being coupled to device coupling 1300. The anchor site may be distal to the lower esophageal sphincter LES, distal to the diaphragm D, and/or any other suitable location.

Figure 2C:
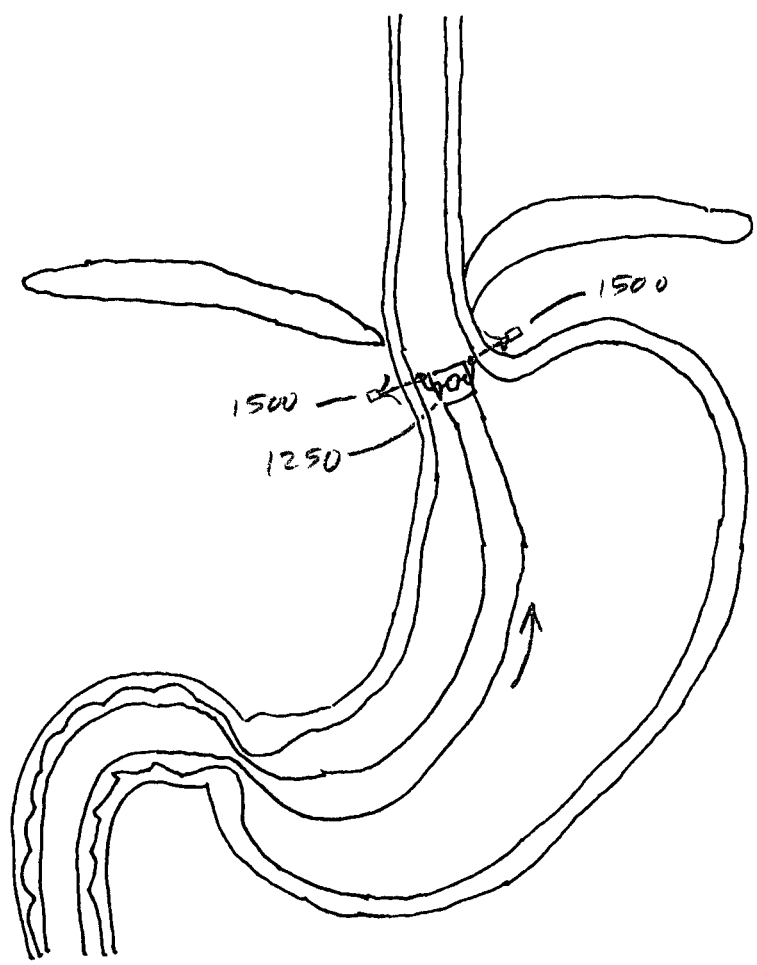

FIG. 2C shows coupling sleeve 1200 to ring 1258. Sleeve coupling 1250 may be pulled proximally and pulled through ring 1258 to couple slots 1257 and ring 1258. Sleeve coupling 1250 may be compressed to aid in pulling through ring 1258. Alternatively, sleeve coupling 1250 may include a drawstring to aid in pulling through ring 1258.

Figure 2D:
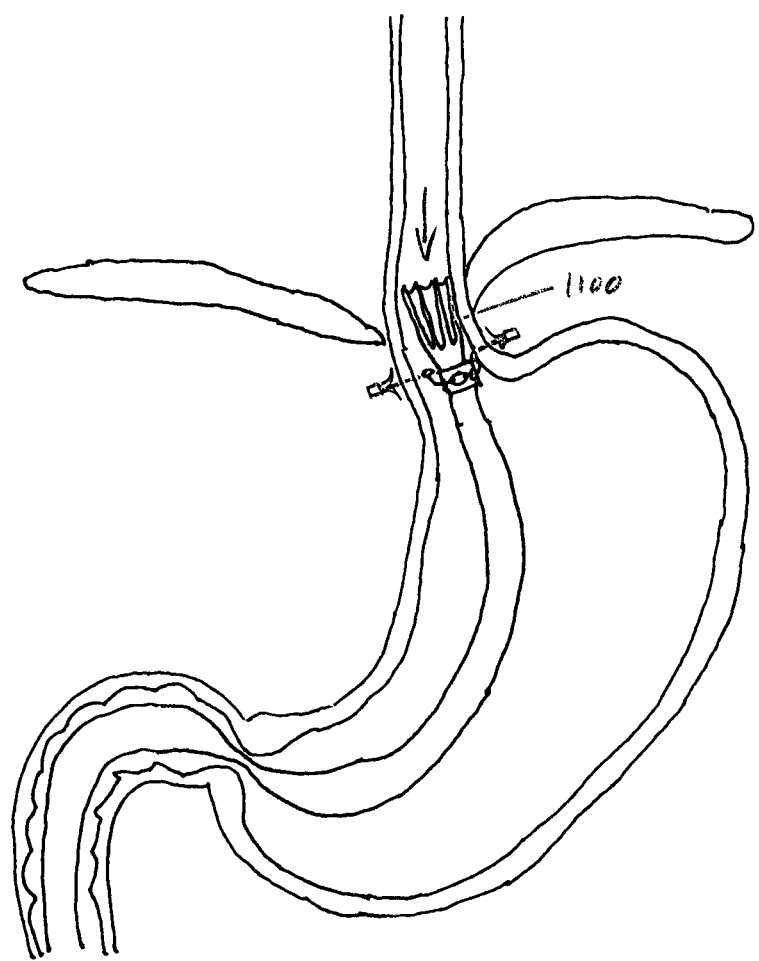

FIG. 2D shows coupling receiver 1100 to sleeve 1200. Clips 1156 may be inserted into spaces 1256 between dimples 1255. Channels 1158 of clips 1156 may be coupled to ring 1258.

Figure 3A:
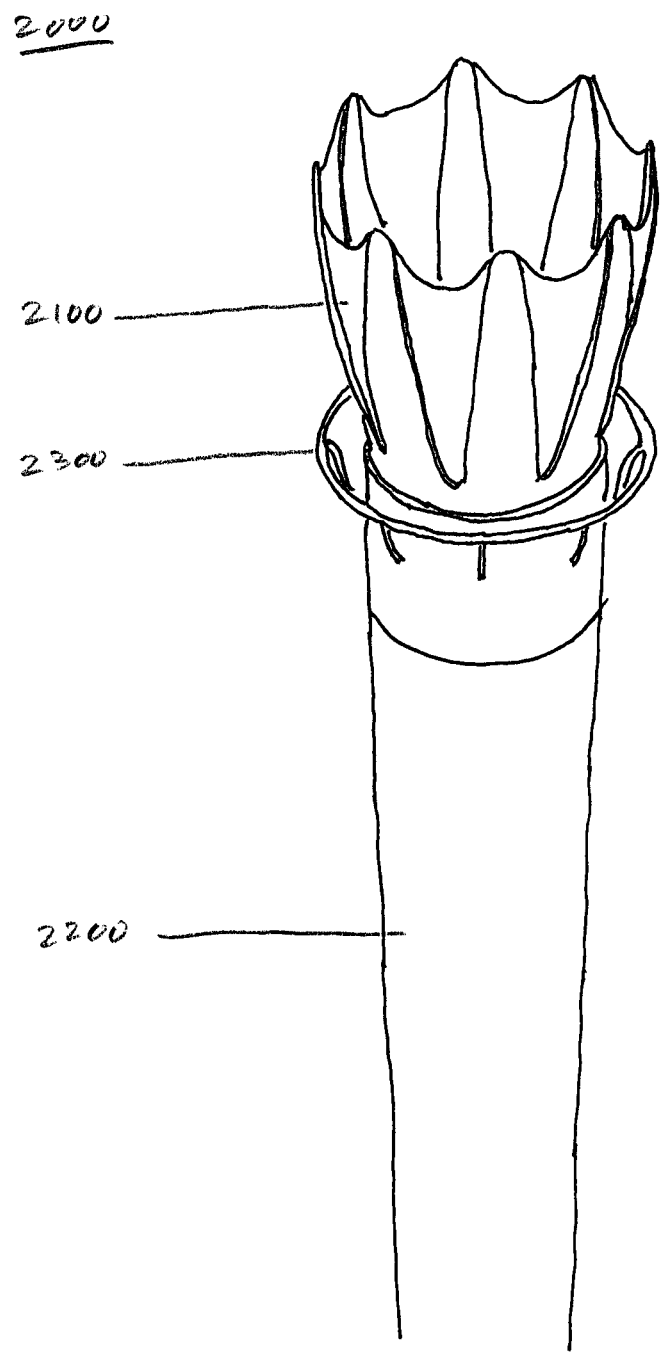
FIGS. 3A-3B show perspective and side views, respectively, of another embodiment of a gastrointestinal bypass device 2000.
Figure 3B:
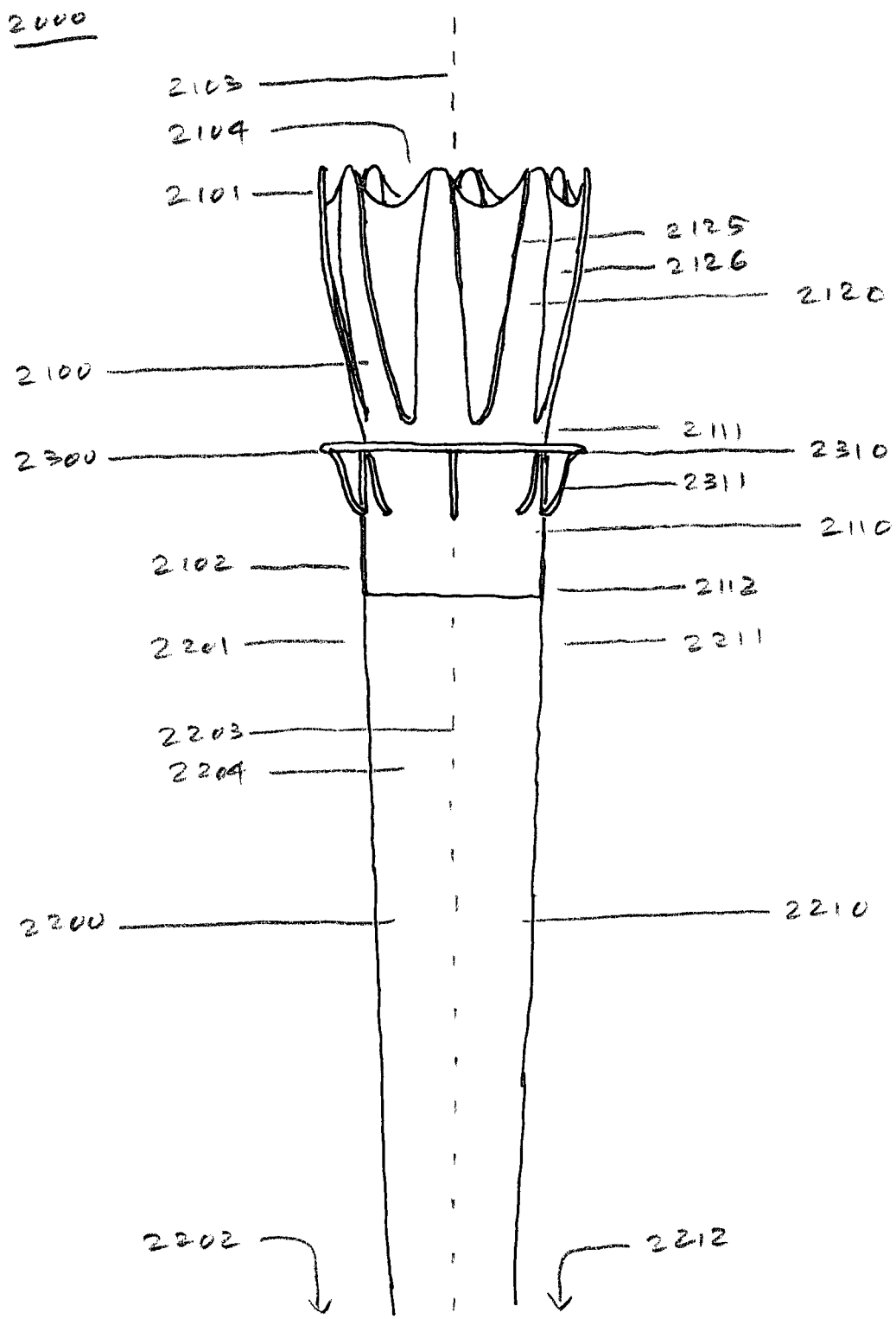
Figure 3C:
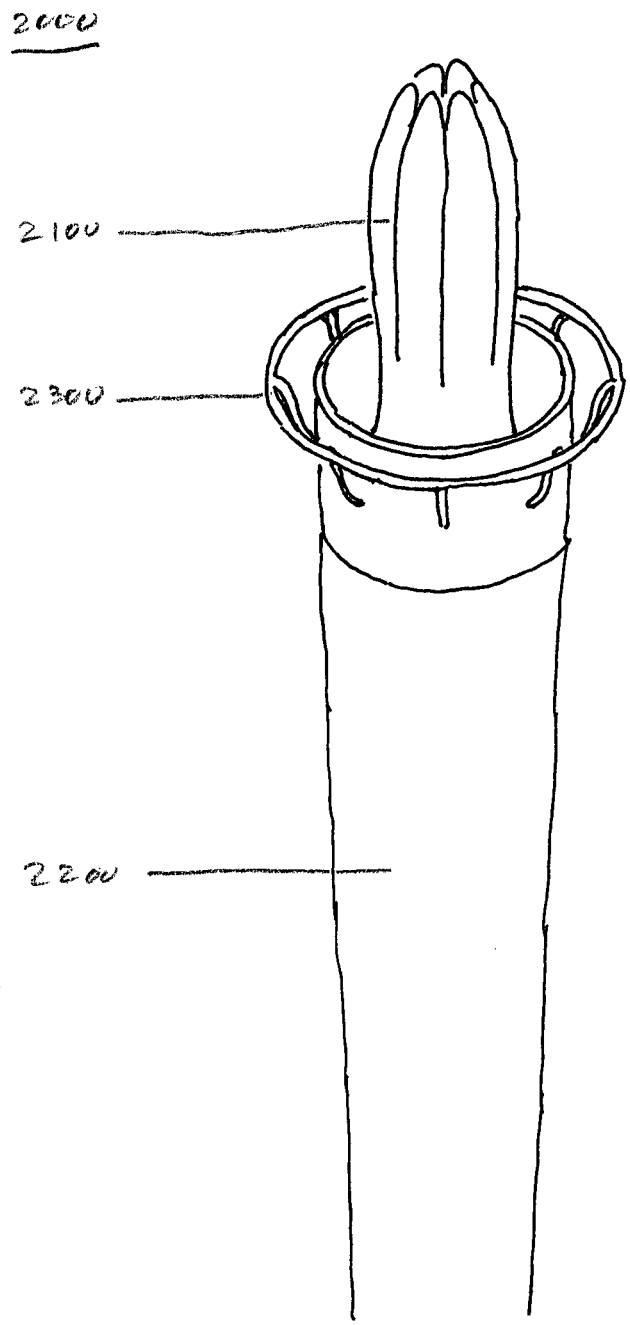
FIG. 3C shows gastrointestinal bypass device 2000 in a closed configuration.
Figure 3D:
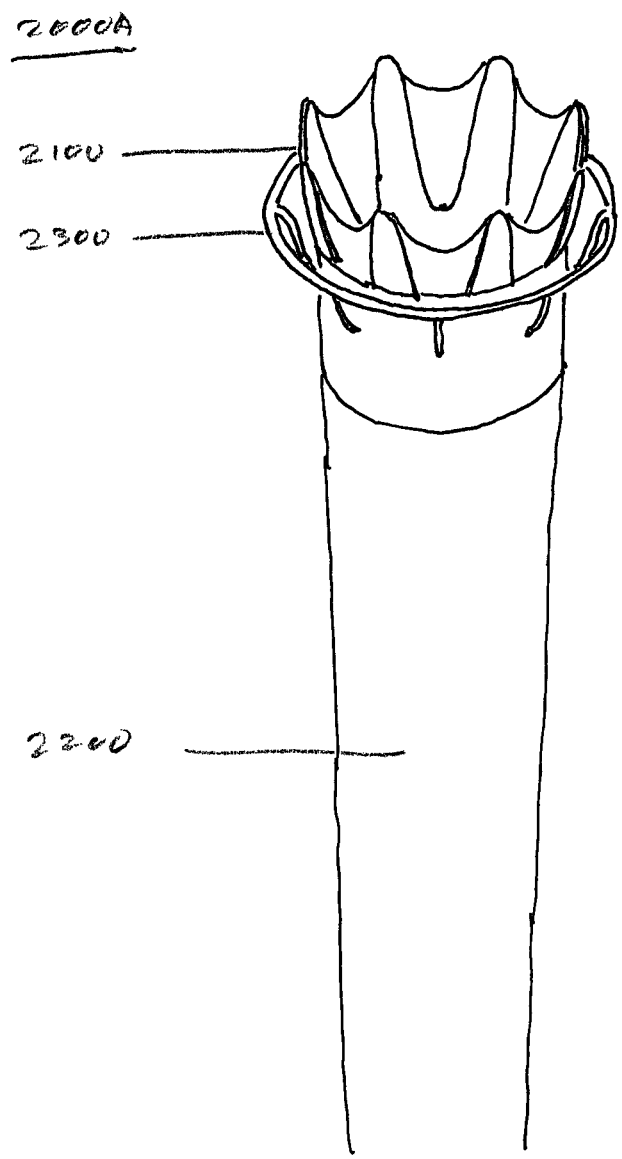
FIGS. 3D-3E show perspective and side views, respectively, of yet another embodiment of gastrointestinal bypass device 2000A.
Figure 3E:
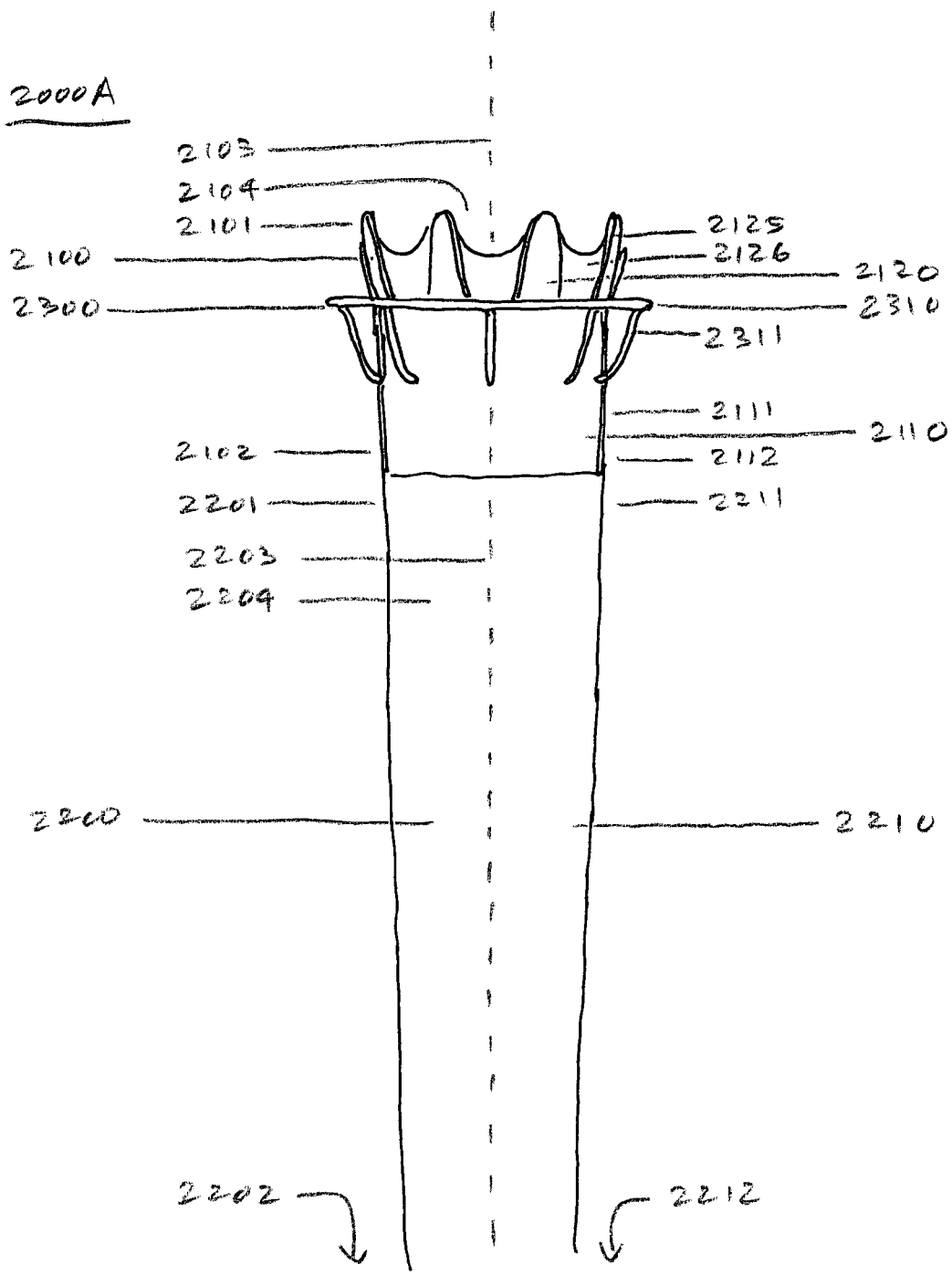
Figure 36:
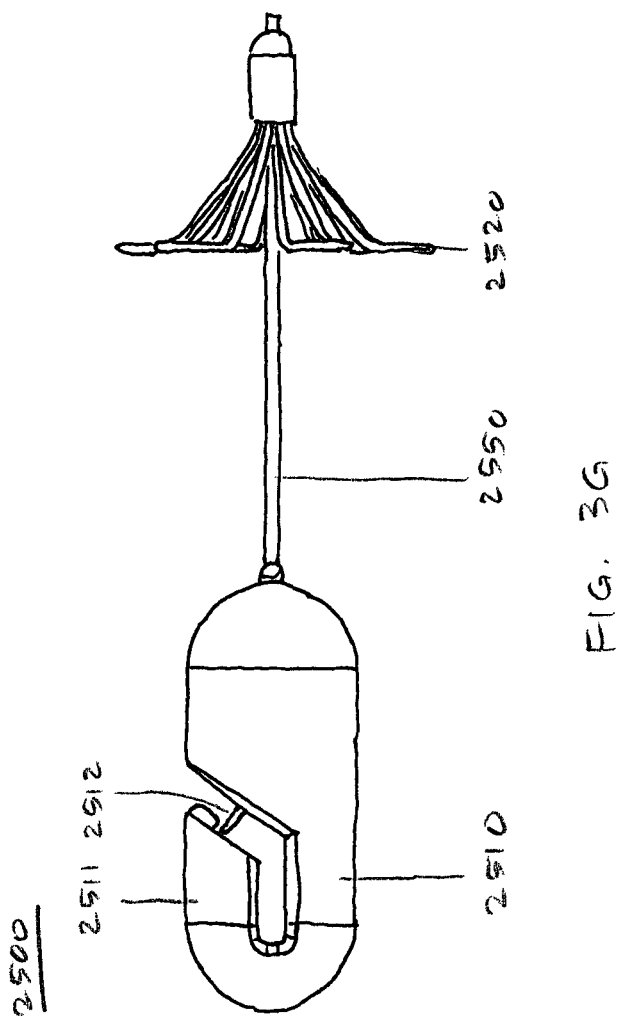

FIGS. 3A-3B show perspective and side views, respectively, of another embodiment of a gastrointestinal bypass device 2000. FIG. 3C shows gastrointestinal bypass device 2000 in a closed configuration. FIGS. 3D-3E show perspective and side views, respectively, of yet another embodiment of gastrointestinal bypass device 2000A.

Gastrointestinal bypass device 2000 and 2000A may be used for directing food and liquids from the esophagus and/or a proximal portion of the stomach into the intestines.

Gastrointestinal bypass device 2000 and 2000A may include a receiver 2100, a sleeve 2200, and a device coupling 2300. Gastrointestinal bypass device 2000 and 2000A may be configured to be used with one or more tissue anchors 2500.

Receiver 2100 may include a proximal portion 2101, a distal portion 2102, a longitudinal axis 2103, and a lumen 2104. Receiver 2100 may be configured to be positioned in the esophagus and/or the stomach. Receiver 2100 may be configured to receive food and liquids from the esophagus and/or a proximal portion of the stomach into lumen 2104. Receiver 2100 may be configured to reduce the amount of food and liquids which pass to an outside of receiver 2100 instead of through lumen 2104. Proximal portion 2101 of receiver 2100 may be configured to open and close to at least partially conform to an inside of the esophagus and/or a proximal portion of the stomach.

Receiver 2100 may include a body 2110 and a plurality of fingers 2120.

Body 2110 may include a proximal portion 2111 and a distal portion 2112. Body 2110 may be configured to be positioned in the esophagus and/or the stomach. Body 2110 may be configured to be positioned distal to the lower esophageal sphincter. Body 2110 may provide support to fingers 2120. Body 2110 may include a ring or a short tubular element. Body 2110 may be flexible. Body 2110 may have sufficient hoop strength to resist radial expansion. Body 2110 may be made of a polyurethane elastomer such as PELLETHANE, silicone, and/or any other suitable material.

Fingers 2120 may extend proximally from proximal portion 2111 of body 2110. Fingers 2120 may be configured to extend at least partially through the lower esophageal sphincter as shown in FIGS. 3A-3B, into a proximal portion of the stomach as shown in FIGS. 3D-3E, above the lower esophageal sphincter, or anywhere in the esophagus. Fingers 2120 may be configured to open and close to at least partially conform to an inside of the esophagus and/or a proximal portion of the stomach. Fingers 2120 may be configured to have an outward bias that is large enough to at least partially conform to an inside of the esophagus and/or a proximal portion of the stomach. Fingers 2120 may be configured to have an outward bias that is small enough not to substantially interfere with the closing or normal functioning of the esophagus and/or a proximal portion of the stomach. Fingers 2120 may use body 2110 as a fulcrum to maintain at least a portion of an outward bias.

Fingers 2120 may have a shape that cooperates with other fingers 2120 when fingers 2120 are closed, as shown in FIG. 3C. Fingers 2120 may have a shape that is sinusoidal, triangular, or any other suitable shape. Fingers 2120 may have a cross section that is flat, cylindrical, or any other suitable cross section. Fingers 2120 may have a uniform or varying thickness. Fingers 2120 may be flexible. Fingers 2120 may be made of a polyurethane elastomer such as PELLETHANE, silicone, and/or any other suitable material.

Fingers 2120 may include one or more stiffening elements 2125 coupled around the edge of fingers 2120. Alternatively, stiffening elements 2125 may be coupled along the center of fingers 2120 and/or any other suitable location. Stiffening elements 2125 may provide at least some support to fingers 2120 to extend proximally. Stiffening elements 2125 may provide at least some outward bias to fingers 2120 to conform to an inside of the esophagus and/or a proximal portion of the stomach. Stiffening elements 2125 may reduce the likelihood of fingers 2120 being inverted distally into lumen 2114, or help allow inverted fingers 1120 to reposition themselves. Stiffening elements 2125 may include a wire, stent, scaffold, thickened portions of fingers 2120, and/or any other suitable element. Stiffening elements 2125 may be made of a metal, plastic, and/or any other suitable material.

Alternatively, stiffening elements 2125 may be similar in part or in whole to one or more of the scaffolds and/or struts described in U.S. patent application Ser. No. 13/485,887 (VALENTX 021A1), which is hereby incorporated by reference in its entirety.

Fingers 2120 may include webbing 2126 coupled between fingers 2120. Webbing 2126 may cover a portion or substantially all of the space between adjacent fingers 2120. Webbing 2126 may reduce the amount of food and liquids leaking out between fingers 2120. Webbing 2126 may be flexible. Webbing 2126 may be stretchable or non-stretchable. Webbing 2126 may be sufficiently thin to reduce bunching when fingers 2120 close. Webbing 2126 may be made of a polyurethane elastomer such as PELLETHANE, silicone, and/or any other suitable material.

Alternatively, receiver 2100 may be any suitably shaped structure, such as a bowl-, cup-, or cone-shaped structure, having a proximal portion configured to open and close to conform to an inside of the esophagus and/or a proximal portion of the stomach, without substantially interfering with the closing or normal functioning of the esophagus and/or a proximal portion of the stomach.

Sleeve 2200 may include a proximal portion 2201, a distal portion 2202, a longitudinal axis 2203, and a lumen 2204. Sleeve 2200 may be coupled to distal portion 2102 of receiver 2100. Sleeve 2200 may be configured to be positioned in the stomach and the intestines. Lumen 2204 of sleeve 2200 may be in communication with lumen 2104 of receiver 2100. Sleeve 2200 may be configured to direct food and liquids from receiver 2100 into the intestines.

Sleeve 2200 may include a tube 2210. Tube 2210 may include a proximal portion 2211 and a distal portion 2212. Tube 2210 may be similar in part or in whole to one or more of the tubes described in U.S. patent application Ser. No. 13/485,887 (VALENTX 021A1), which is hereby incorporated by reference in its entirety.

Device coupling 2300 may be coupled to distal portion 2102 of receiver 2100. Alternatively, device coupling 2300 may be coupled to proximal portion 2201 of sleeve 2200. Device coupling 2300 may thus be distanced from proximal portion 2101 of receiver 2100. Distancing device coupling 2300 from proximal portion 2101 of receiver 2100 serves to separate the function of coupling to tissue anchors 2500 and the function of conforming to the inside of the esophagus and/or proximal portion of the stomach. This also allows the option of delivering tissue anchors 2500 below the lower esophageal sphincter while having receiver 2100 extend into or proximal to the lower esophageal sphincter. This also allows for greater variation in the lengths of the tension element in the tissue anchors.

Device coupling 2300 may be configured to be removably or irremovably coupled to tissue anchors 2500. Device coupling 2300 may include a halo 2310. Halo 2310 may be coupled to distal portion 2102 of receiver 2100 and/or proximal portion of 2201 sleeve 2200. Halo 2310 may be coupled with a plurality of standoffs 2311.

Alternatively, device coupling 2300 may be similar in part or in whole to one or more of the device couplings described in U.S. provisional patent application Ser. No. 61/756,366 (VALENTX 024), which is hereby incorporated by reference in its entirety.

One or more elements of gastrointestinal bypass device 2000 and 2000A may be formed integrally as a single piece, using one or more materials. For example, receiver 2100, sleeve 2200, and device coupling 3200 may be formed integrally as a single piece. As another example, receiver 2100 and sleeve 2200 may be formed integrally as a single piece, with the exception of webbing 2126 between fingers 2120, which may be added on later.

FIGS. 3F-3G show perspective and side views, respectively, of one embodiment of a tissue anchor 2500. Tissue anchor 2500 may include an anchor coupling 2510, a distal retention element 2520, and a tension element 2550.

Anchor coupling 2510 may be configured to be coupled to device coupling 2300. Anchor coupling 2510 may include a hook 2511. Hook 2511 may include a retainer 2512 configured to retain halo 2310 once coupled to hook 2511.

Distal retention element 2520 may be configured to be deployed outside of a wall of the esophagus and/or a proximal portion of the stomach. Distal retention element 2520 may be similar in part or in whole to one or more of the distal retention elements described in the following, which are hereby incorporated by reference in their entireties: U.S. Pat. No. 8,070,743 (VALTX.001CP2); U.S. patent application Ser. No. 12/137,473 (VALTX.020A), Ser. No. 13/485,887 (VALENTX 021A1), and Ser. No. 13/743,287 (VALENTX 021CP2); U.S. provisional patent application Ser. No. 61/756,366 (VALENTX 024).

Tension element 2550 may include a proximal portion 2551 and a distal portion 2552. Proximal portion 2551 of tension element 2550 may be fixedly or adjustably coupled to anchor coupling 2510. Distal portion 2552 of tension element 2550 may be fixedly or adjustably coupled to distal retention element 2520. Tension element 2550 may be configured to pass through a wall of the esophagus and/or a proximal portion of the stomach.

Alternatively, tissue anchor 2500 may be similar in part or in whole to one or more of the tissue anchors described in the following, which are hereby incorporated by reference in their entireties: U.S. Pat. No. 8,070,743 (VALTX.001CP2); U.S. patent application Ser. No. 12/137,473 (VALTX.020A), Ser. No. 13/485,887 (VALENTX 021A1), and Ser. No. 13/743,287 (VALENTX 021CP2); U.S. provisional patent application Ser. No. 61/756,366 (VALENTX 024).

Figure 4A:
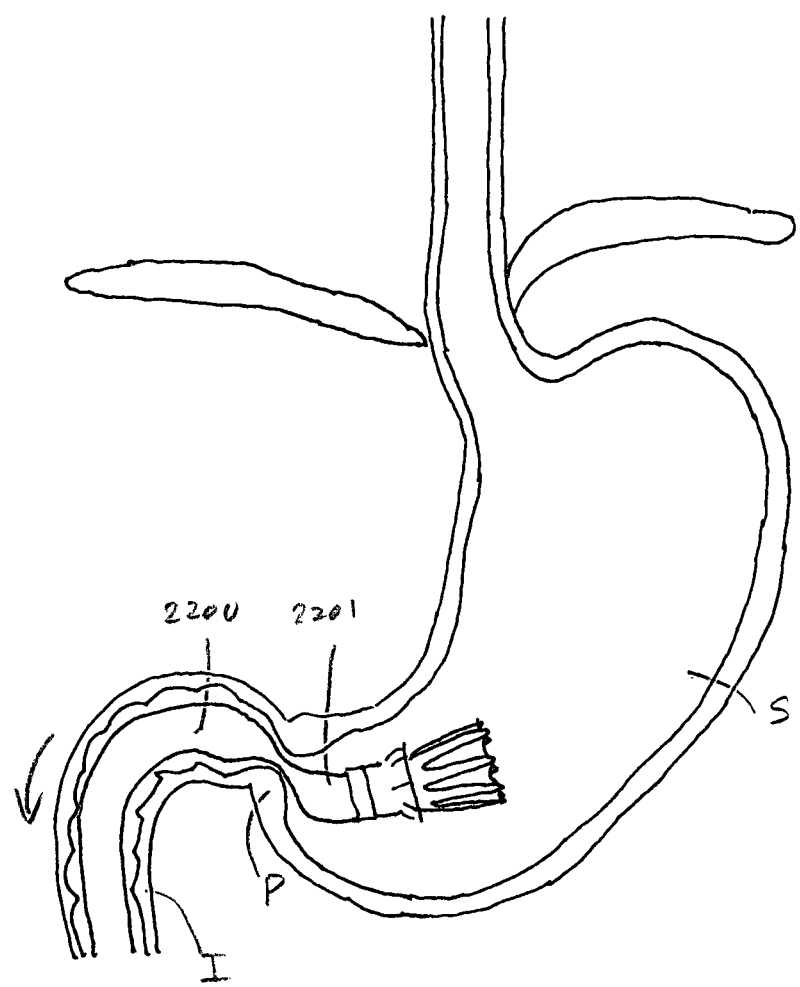
FIGS. 4A-4C show one embodiment of a method for delivering gastrointestinal bypass device 2000 or 2000A.
Figure 4B:
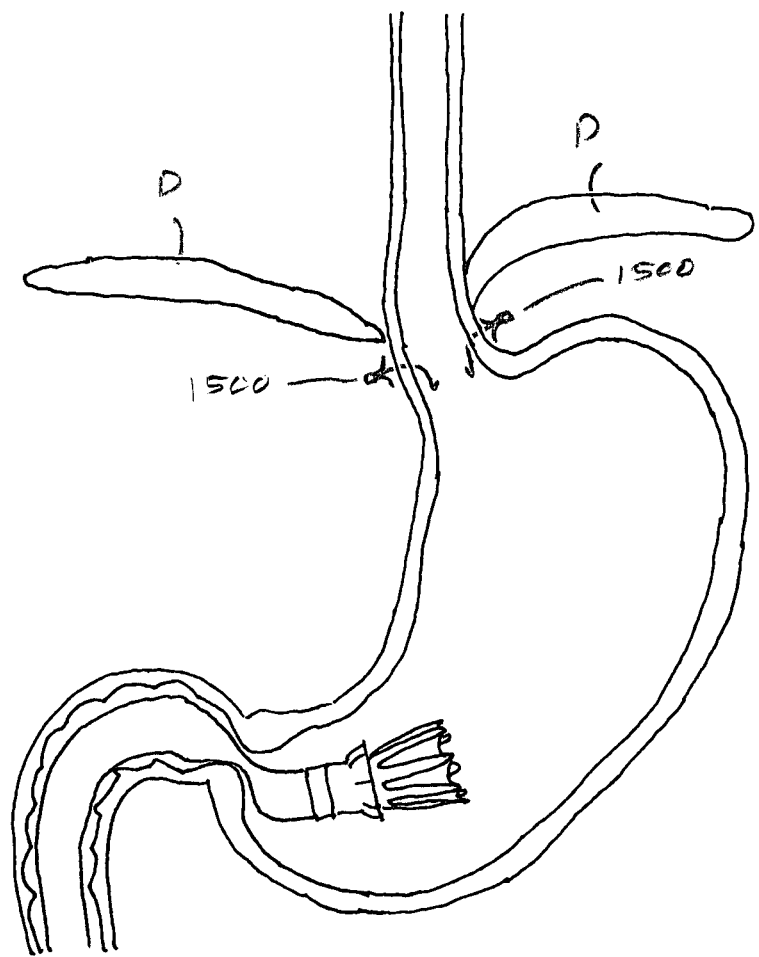
Figure 4C:
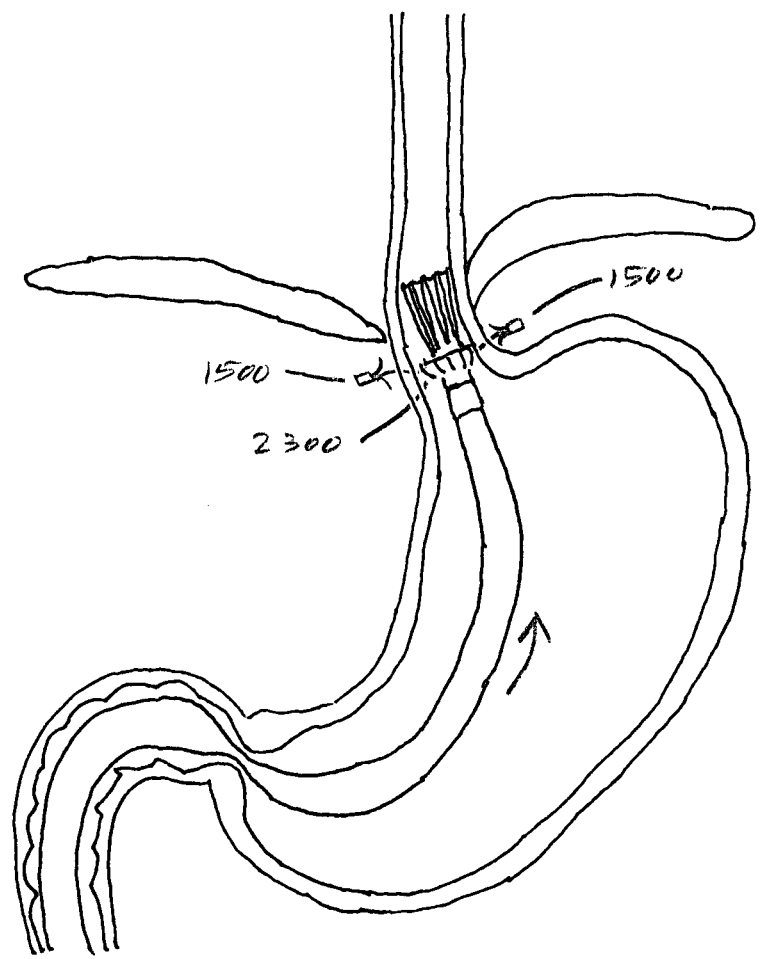

FIGS. 4A-4C show one embodiment of a method for delivering gastrointestinal bypass device 2000 or 2000A. Sleeve 2200 may first be loaded onto a sleeve delivery device.

The sleeve delivery device may be similar in part or in whole to one or more of the sleeve delivery devices described in U.S. patent application Ser. No. 13/485,887 (VALENTX 021A1), which is hereby incorporated by reference in its entirety.

FIG. 4A shows positioning proximal portion 2201 of sleeve 2200 at or near the pylorus P. Sleeve 2200 is then deployed into the intestines I.

The anchor site may first be marked using a tissue marking device before tissue anchors 2500 are delivered to aid in placement of tissue anchors 2500. The tissue marking device may be similar in part or in whole to one or more of the tissue marking devices described in U.S. patent application Ser. No. 13/485,887 (VALENTX 021A1), which is hereby incorporated by reference in its entirety.

FIG. 4B shows delivering tissue anchors 2500 through the wall of the esophagus E and/or a proximal portion of the stomach S at the anchor site. The anchor site may be distal to the lower esophageal sphincter LES, distal to the diaphragm D, and/or any other suitable location.

FIG. 4C shows coupling device coupling 2300 to tissue anchors 2500. Gastrointestinal bypass device 2000 or 2000A may be pulled proximally to couple device coupling 2300 to tissue anchors 2500.

Figure 4D:
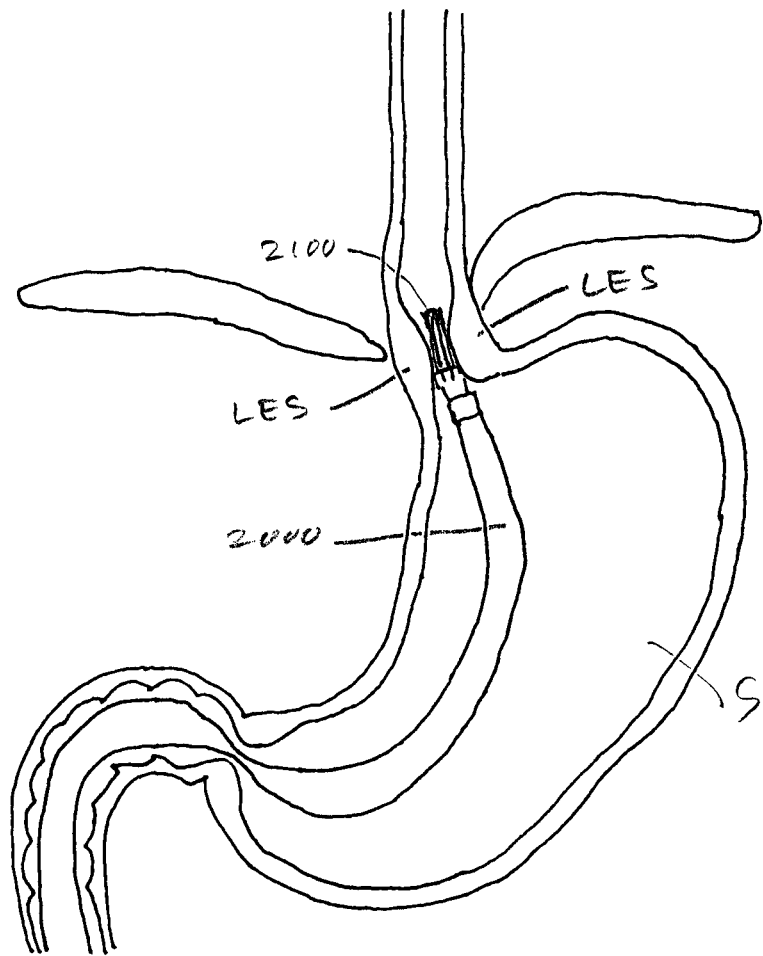
FIG. 4D shows gastrointestinal bypass device 2000 with the lower esophageal sphincter LES at least partially closed.
Figure 4E:
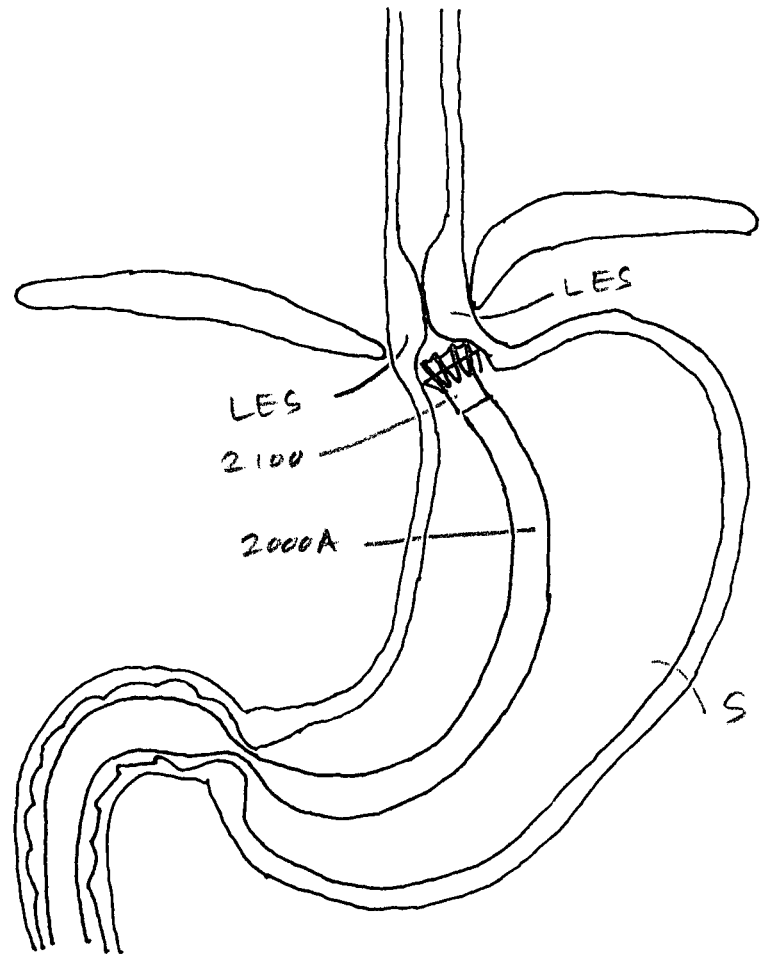
FIG. 4E shows gastrointestinal bypass device 2000A with the lower esophageal sphincter LES at least partially closed.

FIG. 4D shows gastrointestinal bypass device 2000 with the lower esophageal sphincter LES at least partially closed. Receiver 2100 extends at least partially through the lower esophageal sphincter LES. FIG. 4E shows gastrointestinal bypass device 2000A with the lower esophageal sphincter LES at least partially closed. Receiver 2100 extends into a proximal portion of the stomach S.

Figure 5A:
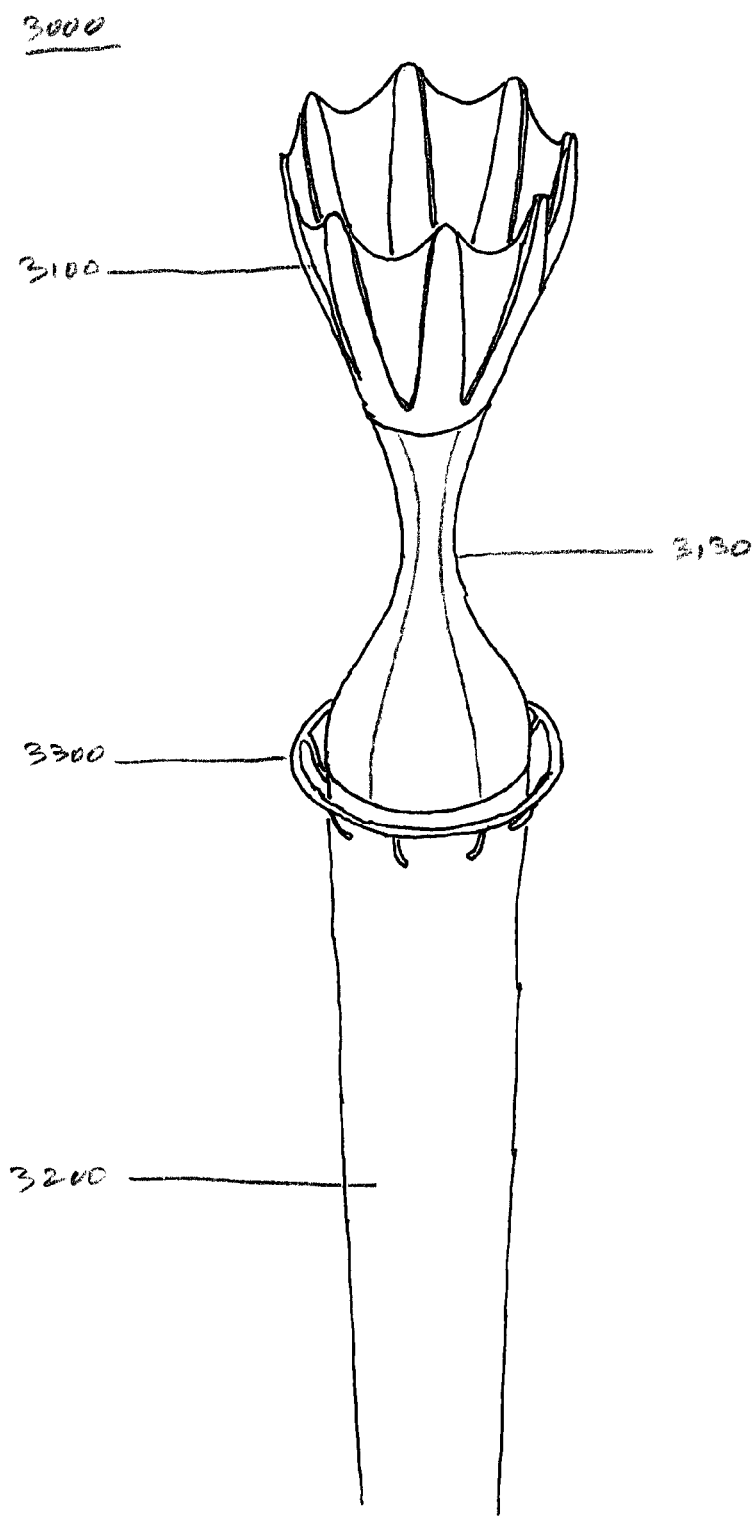
FIGS. 5A-5B show perspective and side views, respectively, of still another embodiment of a gastrointestinal bypass device 3000.
Figure 5B:
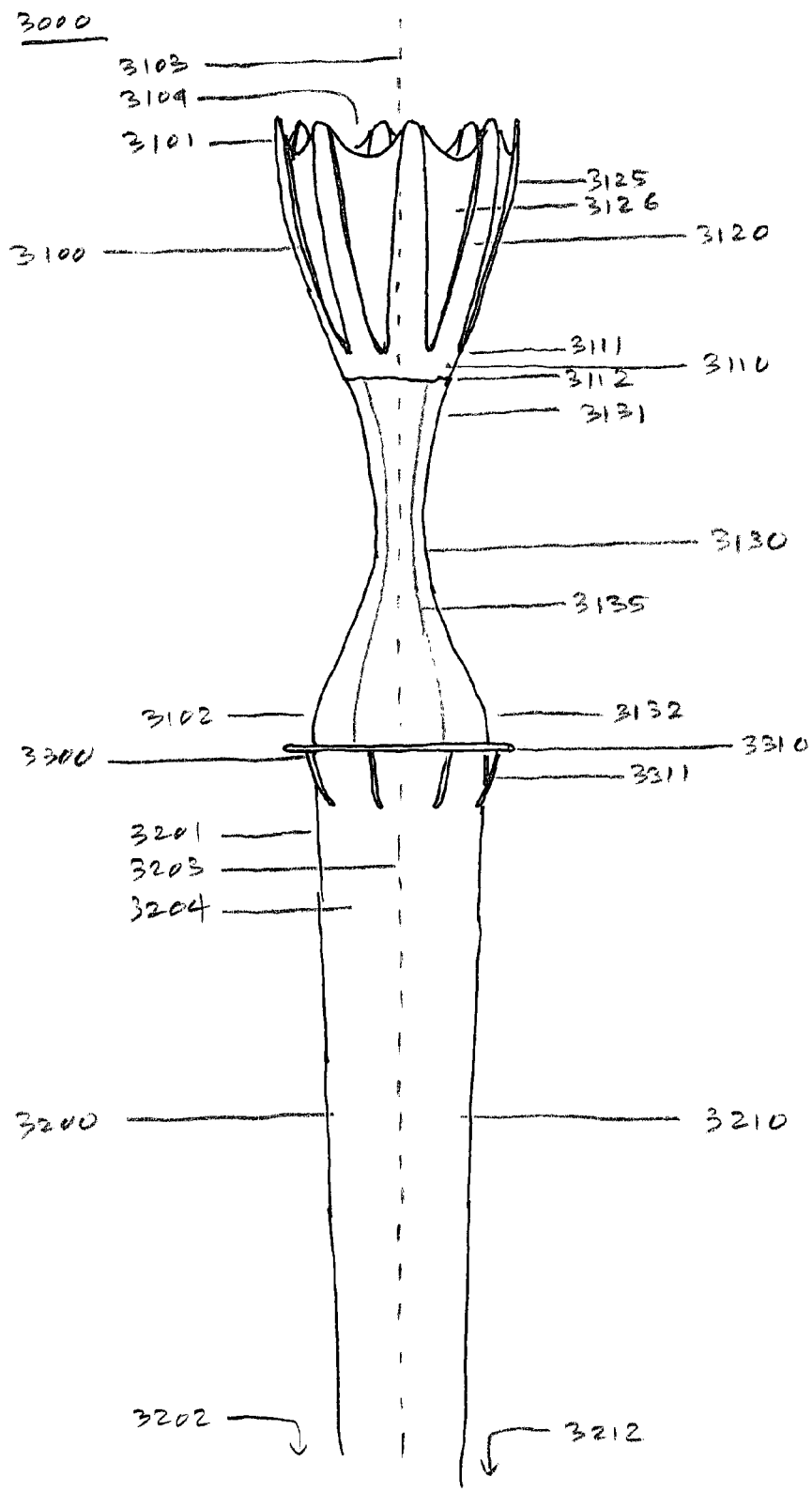

FIGS. 5A-5B show perspective and side views, respectively, of still another embodiment of a gastrointestinal bypass device 3000.

Gastrointestinal bypass device 3000 may be used for directing food and liquids from the esophagus into the intestines.

Gastrointestinal bypass device 3000 may include a receiver 3100, a sleeve 3200, and a device coupling 3300. Gastrointestinal bypass device 3000 may be configured to be used with one or more tissue anchors 3500.

Receiver 3100 may include a proximal portion 3101, a distal portion 3102, a longitudinal axis 3103, and a lumen 3104. Receiver 3100 may be configured to be positioned in the esophagus and/or the stomach. Receiver 3100 may be configured to receive food and liquids from the esophagus into lumen 3104. Receiver 3100 may be configured to reduce the amount of food and liquids which pass to an outside of receiver 3100 instead of through lumen 3104. Proximal portion 3101 of receiver 3100 may be configured to open and close to at least partially conform to an inside of the esophagus.

Receiver 3100 may include a body 3110, a plurality of fingers 3120, and an extension 3130.

Body 3110 may include a proximal portion 3111 and a distal portion 3112. Body 3110 may be configured to be positioned in the esophagus proximal to the lower esophageal sphincter. Body 3110 may provide support to fingers 3120. Body 3110 may include a ring or a short tubular element. Body 3110 may be flexible. Body 3110 may have sufficient hoop strength to resist radial expansion. Body 3110 may be made of a polyurethane elastomer such as PELLETHANE, silicone, and/or any other suitable material.

Fingers 3120 may extend proximally from proximal portion 3111 of body 3110. Fingers 3120 may be configured to extend into the esophagus. Fingers 3120 may be configured to open and close to at least partially conform to an inside of the esophagus. Fingers 3120 may be configured to have an outward bias that is large enough to at least partially conform to an inside of the esophagus. Fingers 3120 may be configured to have an outward bias that is small enough not to substantially interfere with the closing or normal functioning of the esophagus. Fingers 3120 may use body 3110 as a fulcrum to maintain at least a portion of an outward bias.

Fingers 3120 may have a shape that cooperates with other fingers 3120 when fingers 3120 are closed. Fingers 3120 may have a shape that is sinusoidal, triangular, or any other suitable shape. Fingers 3120 may have a cross section that is flat, cylindrical, or any other suitable cross section. Fingers 3120 may have a uniform or varying thickness. Fingers 3120 may be flexible. Fingers 3120 may be made of a polyurethane elastomer such as PELLETHANE, silicone, and/or any other suitable material.

Fingers 3120 may include one or more stiffening elements 3125 coupled around the edge of fingers 3120. Alternatively, stiffening elements 3125 may be coupled along the center of fingers 3120 and/or any other suitable location. Stiffening elements 3125 may provide at least some support to fingers 3120 to extend proximally. Stiffening elements 3125 may provide at least some outward bias to fingers 3120 to conform to an inside of the esophagus. Stiffening elements 3125 may reduce the likelihood of fingers 3120 being inverted distally into lumen 3114, or help allow inverted fingers 1120 to reposition themselves. Stiffening elements 3125 may include a wire, stent, scaffold, thickened portions of fingers 3120, and/or any other suitable element. Stiffening elements 3125 may be made of a metal, plastic, and/or any other suitable material.

Alternatively, stiffening elements 3125 may be similar in part or in whole to one or more of the scaffolds and/or struts described in U.S. patent application Ser. No. 13/485,887 (VALENTX 021A1), which is hereby incorporated by reference in its entirety.

Fingers 3120 may include webbing 3126 coupled between fingers 3120. Webbing 3126 may cover a portion or substantially all of the space between adjacent fingers 3120. Webbing 3126 may reduce the amount of food and liquids leaking out between fingers 3120. Webbing 3126 may be flexible. Webbing 3126 may be stretchable or non-stretchable. Webbing 3126 may be sufficiently thin to reduce bunching when fingers 3120 close. Webbing 3126 may be made of a polyurethane elastomer such as PELLETHANE, silicone, and/or any other suitable material.

Extension 3130 may include a proximal portion 3131 and a distal portion 3132. Extension 3130 may be coupled to distal portion 3112 of body 3110. Extension 3130 may be configured to be positioned at least partially through the lower esophageal sphincter. Extension 3130 may support body 3110 and fingers 3120 at least partially above the lower esophageal sphincter. Extension 3130 may include a tubular structure. Extension 3130 may have a uniform or varying diameter, such as hourglass-shaped.

Extension 3130 may have sufficient column strength to support body 3110 and fingers 3120 at least partially above the lower esophageal sphincter. Extension 3130 may be configured not to substantially interfere with the closing of the esophagus and/or the lower esophageal sphincter, and/or prevent the substantially normal functioning of esophagus and/or the lower esophageal sphincter. Extension 3130 may be sufficiently thin to reduce bunching when the esophagus and/or the lower esophageal sphincter closes. Extension 3130 may be made of a polyurethane elastomer such as PELLETHANE, silicone, and/or any other suitable material.

Extension 3130 may include one or more stiffening elements 3135. Stiffening elements 3135 may be coupled along an inside, outside, or between layers of extension 3130. Stiffening elements 3135 may provide at least some column strength to extension 3130. Stiffening elements 3135 may include a wire, stent, scaffold, thickened portions of extension 3130, and/or any other suitable element. Stiffening element 3135 may be made of a metal, plastic, and/or any other suitable material. Stiffening elements 3135 of extension 3130 may be integral with or discrete from stiffening elements 3125 of fingers 3120.

Alternatively, stiffening elements 3135 may be similar in part or in whole to one or more of the scaffolds and/or struts described in U.S. patent application Ser. No. 13/485,887 (VALENTX 021A1), which is hereby incorporated by reference in its entirety.

Alternatively, receiver 3100 may be any suitably shaped structure, such as a bowl-, cup-, or cone-shaped structure, having a proximal portion configured to open and close to conform to an inside of the esophagus, without substantially interfering with the closing or normal functioning of the esophagus.

Sleeve 3200 may include a proximal portion 3201, a distal portion 3202, a longitudinal axis 3203, and a lumen 3204. Sleeve 3200 may be coupled to distal portion 3102 of receiver 3100. Sleeve 3200 may be configured to be positioned in the stomach and the intestines. Lumen 3204 of sleeve 3200 may be in communication with lumen 3104 of receiver 3100. Sleeve 3200 may be configured to direct food and liquids from receiver 3100 into the intestines.

Sleeve 3200 may include a tube 3210. Tube 3210 may include a proximal portion 3211 and a distal portion 3212. Tube 3210 may be similar in part or in whole to one or more of the tubes described in U.S. patent application Ser. No. 13/485,887 (VALENTX 021A1), which is hereby incorporated by reference in its entirety.

Device coupling 3300 may be coupled to distal portion 3102 of receiver 3100. Alternatively, device coupling 3300 may be coupled to proximal portion 3201 of sleeve 3200. Device coupling 3300 may thus be distanced from proximal portion 3101 of receiver 3100. Distancing device coupling 3300 from proximal portion 3101 of receiver 3100 serves to separate the function of coupling to tissue anchors 3500 and the function of conforming to the inside of the esophagus. This also allows the option of delivering tissue anchors 3500 below the lower esophageal sphincter while having receiver 3100 extend proximal to the lower esophageal sphincter. This also allows for greater variation in the lengths of the tension element in the tissue anchors.

Device coupling 3300 may be configured to be removably or irremovably coupled to tissue anchors 3500. Device coupling 3300 may include a halo 3310. Halo 3310 may be coupled to distal portion 3102 of receiver 3100 or proximal portion 3201 of sleeve 3200. Halo 3310 may be coupled with a plurality of standoffs 3311.

Alternatively, device coupling 3300 may be similar in part or in whole to one or more of the device couplings described in U.S. provisional patent application Ser. No. 61/756,366 (VALENTX 024), which is hereby incorporated by reference in its entirety.

One or more elements of gastrointestinal bypass device 3000 may be formed integrally as a single piece, using one or more materials. For example, receiver 3100, sleeve 3200, and device coupling 3300 may be formed integrally as a single piece. As another example, receiver 3100 and sleeve 3200 may be formed integrally as a single piece, with the exception of webbing 3126 between fingers 3120, which may be added on later.

FIG. 5C shows one embodiment of a tissue anchor 3500. Tissue anchor 3500 may include an anchor coupling 3510, a distal retention element 3520, and a tension element 3550.

Anchor coupling 3510 may be configured to be coupled to device coupling 3300. Anchor coupling 3510 may include a hook 3511. Hook 3511 may include one or more prongs 3512. Prongs 3512 may be radially arranged, which may reduce the need to rotate or orient hook 3511 when coupling halo 3310.

Distal retention element 3520 may be configured to be deployed outside of a wall of the esophagus and/or a proximal portion of the stomach. Distal retention element 3520 may be similar in part or in whole to one or more of the distal retention elements described in the following, which are hereby incorporated by reference in their entireties: U.S. Pat. No. 8,070,743 (VALTX.001CP2); U.S. patent application Ser. No. 12/137,473 (VALTX.020A), Ser. No. 13/485,887 (VALENTX 021A1), and Ser. No. 13/743,287 (VALENTX 021CP2); U.S. provisional patent application Ser. No. 61/756,366 (VALENTX 024).

Tension element 3550 may include a proximal portion 3551 and a distal portion 3552. Proximal portion 3551 of tension element 3550 may be fixedly or adjustably coupled to anchor coupling 3510. Distal portion 3552 of tension element 3550 may be fixedly or adjustably coupled to distal retention element 3520. Tension element 3550 may be configured to pass through a wall of the esophagus and/or a proximal portion of the stomach.

Alternatively, tissue anchor 3500 may be similar in part or in whole to one or more of the tissue anchors described in the following, which are hereby incorporated by reference in their entireties: U.S. Pat. No. 8,070,743 (VALTX.001CP2); U.S. patent application Ser. No. 12/137,473 (VALTX.020A), Ser. No. 13/485,887 (VALENTX 021A1), and Ser. No. 13/743,287 (VALENTX 021CP2); U.S. provisional patent application Ser. No. 61/756,366 (VALENTX 024).

Figure 6A:
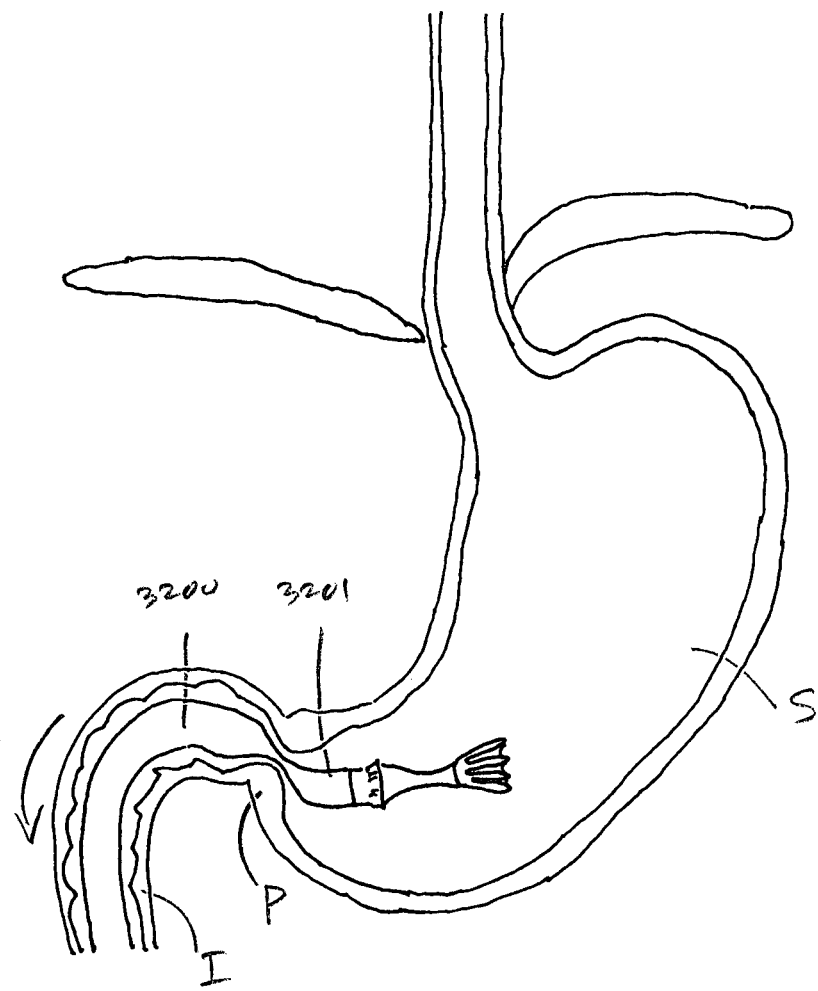
FIGS. 6A-6C show one embodiment of a method for delivering gastrointestinal bypass device 3000.
Figure 6B:
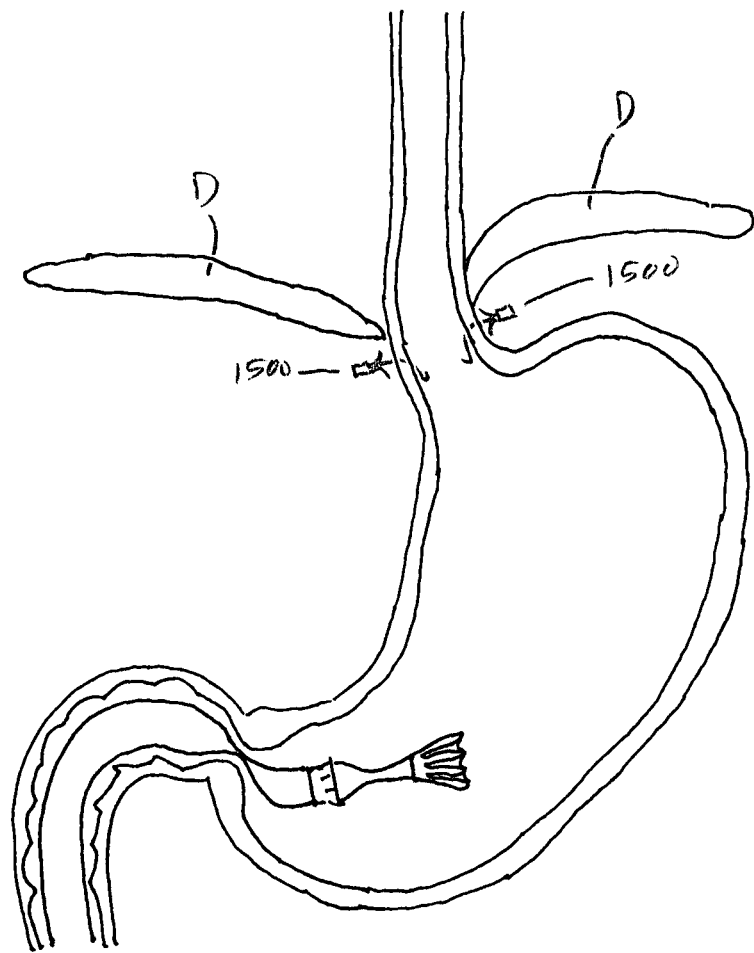
Figure 6C:
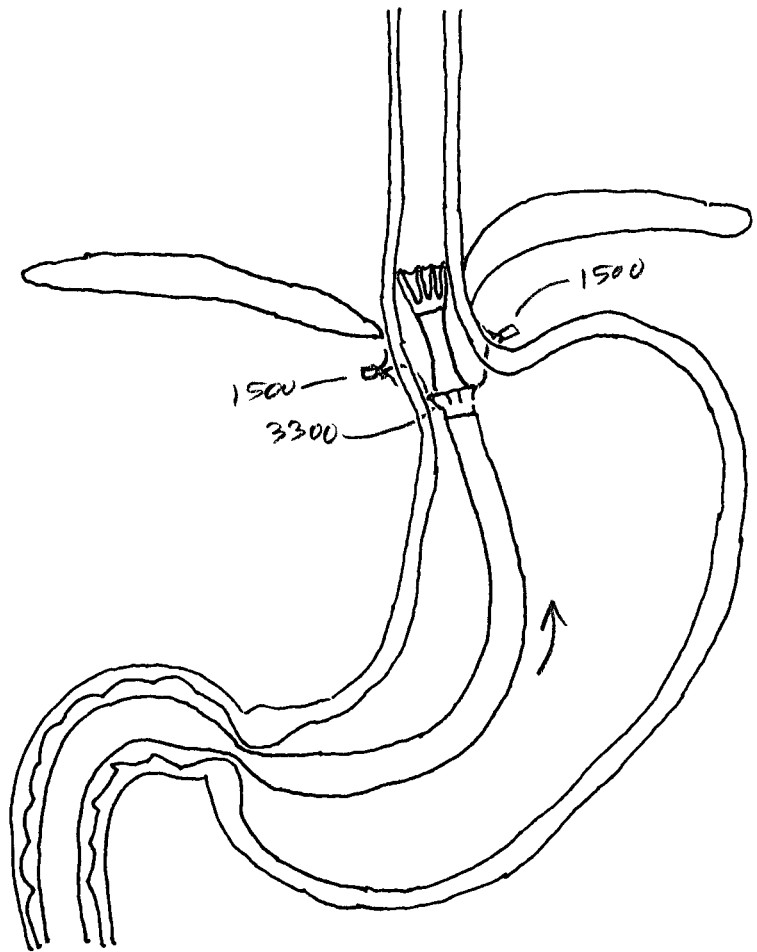

FIGS. 6A-6C show one embodiment of a method for delivering gastrointestinal bypass device 3000. Sleeve 3200 may first be loaded onto a sleeve delivery device.

The sleeve delivery device may be similar in part or in whole to one or more of the sleeve delivery devices described in U.S. patent application Ser. No. 13/485,887 (VALENTX 021A1), which is hereby incorporated by reference in its entirety.

FIG. 6A shows positioning proximal portion 3201 of sleeve 3200 at or near the pylorus P. Sleeve 3200 is then deployed into the intestines I.

The anchor site may first be marked using a tissue marking device before tissue anchors 3500 are delivered to aid in placement of tissue anchors 3500. The tissue marking device may be similar in part or in whole to one or more of the tissue marking devices described in U.S. patent application Ser. No. 13/485,887 (VALENTX 021A1), which is hereby incorporated by reference in its entirety.

FIG. 6B shows delivering tissue anchors 3500 through the wall of the esophagus E and/or a proximal portion of the stomach S at the anchor site. The anchor site may be distal to the lower esophageal sphincter LES, distal to the diaphragm D, and/or any other suitable location.

FIG. 6C shows coupling device coupling 3300 to tissue anchors 3500. Gastrointestinal bypass device 3000 may be pulled proximally to couple device coupling 3300 to tissue anchors 3500.

Figure 6D:
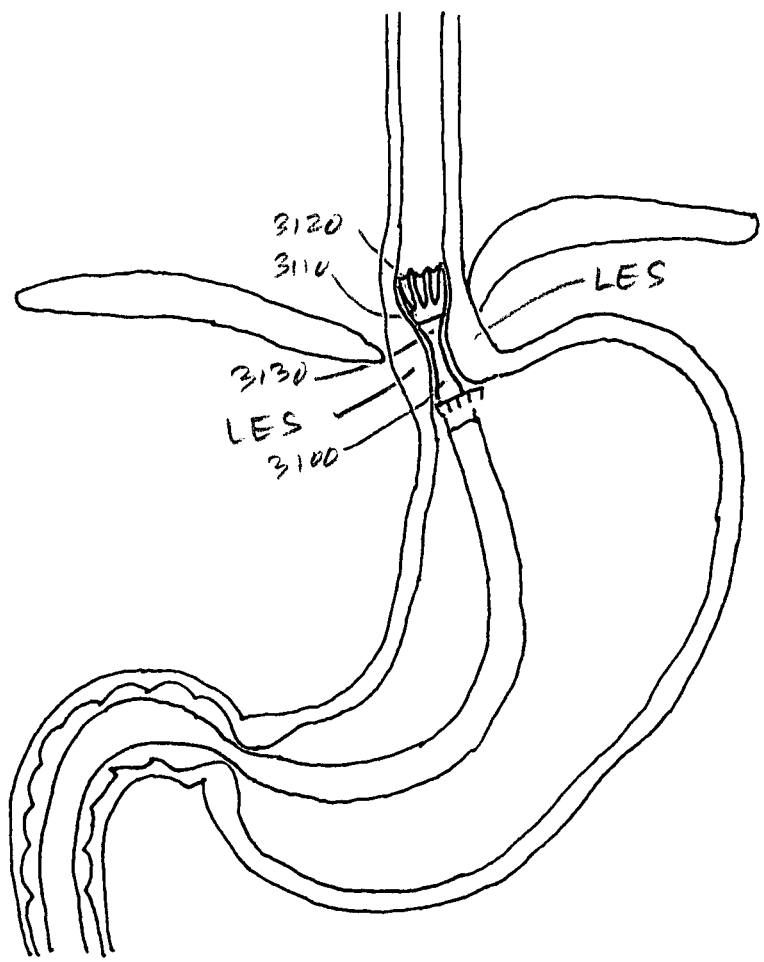
FIG. 6D shows gastrointestinal bypass device 3000 with the lower esophageal sphincter LES at least partially closed.

FIG. 6D shows gastrointestinal bypass device 3000 with the lower esophageal sphincter LES at least partially closed. Receiver 3100 extends at least partially through the lower esophageal sphincter LES. Extension 3130 supports body 3110 and fingers 3120 at least partially above the lower esophageal sphincter LES.

While the foregoing has been with reference to particular embodiments of the invention, it will be appreciated by those skilled in the art that changes in these embodiments may be made without departing from the principles and spirit of the invention, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A gastrointestinal bypass device for directing food and liquids from an esophagus and/or a proximal portion of a stomach into an intestines, the device comprising:
   a receiver configured to be positioned in the esophagus and/or the stomach, a proximal portion of the receiver configured to open and close to at least partially conform to an inside of the esophagus and/or a proximal portion of the stomach, the receiver configured to receive food and liquids from the esophagus and/or a proximal portion of the stomach into a lumen of the receiver; and
   a sleeve coupled to a distal portion of the receiver, the sleeve configured to be positioned in the stomach and the intestines, the sleeve having a lumen in communication with the lumen of the receiver, the sleeve configured to direct the food and the liquids from the receiver into the intestines; and
   a device coupling coupled by a standoff to the distal portion of the receiver and/or a proximal portion of the sleeve, the device coupling configured to be coupled to one or more tissue anchors.

2. The device of claim 1, wherein the receiver comprises a body and a plurality of fingers extending proximally from a proximal portion of the body.

3. The device of claim 2, wherein the fingers have an outward bias that is large enough to at least partially conform to an inside of the esophagus and/or a proximal portion of the stomach.

4. The device of claim 2, wherein the fingers have an outward bias that is small enough not to substantially interfere with the closing or normal functioning of the esophagus and/or a proximal portion of the stomach.

5. The device of claim 2, wherein the receiver further comprises one or more stiffening elements coupled to the fingers.

6. The device of claim 2, wherein the receiver further comprises webbing between the fingers.

7. The device of claim 2, wherein the receiver further comprises a receiver coupling coupled to a distal portion of the body.

8. The device of claim 7, wherein the receiver coupling includes one or more clips.

9. The device of claim 7, wherein the sleeve comprises a sleeve coupling configured to be coupled to the device coupling.

10. The device of claim 9, wherein the sleeve coupling includes a ring configured to be coupled to the clips.

11. The device of claim 2, wherein the receiver includes an extension coupled to a distal portion of the body.

12. The device of claim 1, wherein the device coupling includes a loop.

13. The device of claim 1, wherein the device coupling includes a halo.

* * * * *